(12) United States Patent
Fertala et al.

(10) Patent No.: US 9,777,055 B2
(45) Date of Patent: Oct. 3, 2017

(54) ENGINEERED ANTIBODY FOR INHIBITION OF FIBROSIS

(71) Applicant: THOMAS JEFFERSON UNIVERSITY, Philadelphia, PA (US)

(72) Inventors: Andrzej Fertala, Voorhees, NJ (US); Andrzej Steplewski, Phoenixville, PA (US)

(73) Assignee: Thomas Jefferson University, Philadelphia, PA (US)

( * ) Notice: Subject to any disclaimer, the term of this patent is extended or adjusted under 35 U.S.C. 154(b) by 106 days.

(21) Appl. No.: 14/391,585

(22) PCT Filed: Feb. 26, 2013

(86) PCT No.: PCT/US2013/027787
§ 371 (c)(1),
(2) Date: Oct. 9, 2014

(87) PCT Pub. No.: WO2013/158217
PCT Pub. Date: Oct. 24, 2013

(65) Prior Publication Data
US 2015/0071926 A1 Mar. 12, 2015

Related U.S. Application Data

(60) Provisional application No. 61/636,073, filed on Apr. 20, 2012.

(51) Int. Cl.
| C07K 16/00 | (2006.01) |
| C07K 16/46 | (2006.01) |
| C07K 16/28 | (2006.01) |
| C07K 16/18 | (2006.01) |
| A61K 39/00 | (2006.01) |

(52) U.S. Cl.
CPC ........ *C07K 16/18* (2013.01); *A61K 2039/505* (2013.01); *C07K 2317/24* (2013.01); *C07K 2317/565* (2013.01); *C07K 2317/622* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 5,530,101 | A | * | 6/1996 | Queen ................. C07K 16/00 424/133.1 |
| 5,656,439 | A | | 8/1997 | Eyre |
| 5,800,815 | A | * | 9/1998 | Chestnut .......... C07K 14/70564 424/133.1 |
| 6,204,367 | B1 | | 3/2001 | Eyre |
| 6,642,007 | B1 | | 11/2003 | Saltarelli et al. |
| 6,660,481 | B2 | | 12/2003 | Rosenquist et al. |
| 7,365,167 | B2 | | 4/2008 | Watkins et al. |
| 7,390,885 | B2 | | 6/2008 | Watkins et al. |
| 7,566,770 | B2 | | 7/2009 | Watkins et al. |
| 2005/0136428 | A1 | * | 6/2005 | Crea ..................... C07K 16/00 506/11 |
| 2007/0077199 | A1 | | 4/2007 | Watkins et al. |
| 2008/0050388 | A1 | | 2/2008 | Watkins et al. |
| 2008/0131912 | A1 | | 6/2008 | Tu et al. |
| 2009/0104215 | A1 | | 4/2009 | Ekiel et al. |
| 2009/0203037 | A1 | | 8/2009 | Brophy et al. |
| 2009/0252729 | A1 | * | 10/2009 | Farrington ....... A61K 47/48338 424/135.1 |
| 2011/0044896 | A1 | | 2/2011 | Nakamura et al. |

OTHER PUBLICATIONS

Toleikis et al. Cloning single-chain antibody fragments (scFv) from hybridoma cells. Methods in Molecular Medicine, 2004, vol. 94, VIII, 447-458.*
UniProt Direct submission A0N587_9MURI (Jun. 28, 2011) [Retrieved from the Internet Apr. 6, 2013: <http://www.uniprot.org/uniprot/A0N587.txt>].
Steplewski et al, "Inhibition of collagen fibril formation", Fibrogenesis & Tissue Repair, 5(Suppl 1):529 (Jun. 2012).
Fertala et al, "Engineering and Characterization of the Chimeric Antibody that Targets the C-terminal Telopeptide of the a2 Chain of Human Collagen 1: A Next Step in the Quest to Reduce Localized Fibrosis", Connect Tissue Res., (Feb. 22, 2013) [downloaded Apr. 5, 2013 from <http://informahealthcare.com/doi/abs/10.3109/02770903.2013.778839>].
Arakawa et al., "cDNA sequence analysis of monoclonal antibody FU-MK-1 specific for a transmembrane carcinoma-associated antigen, and construction of a mouse/human chimeric antibody", Hybridoma, 18(2):131(8)(Apr. 1999)—(Abstract).
Beger et al, "A Peptide DNA Surrogate Accelerates Autoimmune Manifestations and Nephritis in Lupus-Prone Mice", The Journal of Immunology, 168:3617-3626 (2002).
Chung et al, "Collagen Fibril Formation A New Target to Limit Fibrosis", The Journal of Biological Chemistry, 283(38):25879-25886 (Sep. 19, 2008).
Prockop et al, "Inhibition of the Self-assembly of Collagen I into Fibrils with Synthetic Peptides", The Journal of Biological Chemistry, 273(25):15598-15604 (1998).
Fledelius et al, "Development of a monoclonal antibody to urinary degradation products from the C-terminal telopeptide alpha 1 chain of type I collagen. Application in an enzyme immunoassay and comparison to CrossLaps ELISA", PubMed, Scand J Clin Lab Invest, 57(1):73-83 (Feb. 1997)—(Abstract).
Kirschbaum et al, "The 3' part of the immunoglobulin kappa locus of the mouse", PubMed, 1. Eur J Immunol, 28(5):1458-66 (May 1998)—(Abstract).

(Continued)

*Primary Examiner* — Maher Haddad
(74) *Attorney, Agent, or Firm* — Cozen O'Connor

(57) ABSTRACT

A chimeric, humanized or single-chain antibody contains a light chain variable region containing the complementarity determining regions of SEQ ID NO: 1, SEQ ID NO:2 and SEQ ID NO:3, and a heavy chain variable region containing the complementarity determining regions SEQ ID NO:4, SEQ ID NO:5 and SEQ ID NO:6. The antibody or antibody fragment thereof is capable of binding the C-terminal telopeptide of the α2(I) chain of human collagen I, and is useful in the treatment of diseases or disorders associated with excessive collagen fibril.

20 Claims, 18 Drawing Sheets

(56) References Cited

OTHER PUBLICATIONS

Srivastava et al, "A new monoclonal antibody ELISA for detection and characterization of C-telopeptide fragments of type I collagen in urine", PubMed, Calcif Tissue Int., 69(6):327-36 ( Dec. 2001)—(Abstract).
Gen Bank: AAL92968.1 (Mar. 23, 2002).
GenBank: AAO73036.1 (Mar. 31, 2003).
GenBank: AAR75704.1 (Dec. 18, 2003).
GenBank: BAA32079.1 (Mar. 27, 2002).
GenBank: CAA75918.1 (Nov. 14, 2006).
GenBank: CAT03374.1 (Dec. 14, 2008).

* cited by examiner

Met Val Leu Met Leu Leu Leu Leu Trp Val Ser Gly Thr Cys
Gly Asp Ile Val Met Ser Gln Ser Pro Ser Ser Leu Ala Val
Ser Ala Gly Glu Lys Val Thr Met Ser Cys Lys Ser Ser Gln
Ser Leu Leu Asn Ser Arg Thr Arg Lys Asn Asn Leu Ala Trp
Tyr Gln Gln Lys Pro Gly Gln Ser Pro Lys Leu Leu Ile Tyr
Trp Ala Ser Thr Arg Glu Ser Gly Val Pro Asp Arg Phe Thr
Gly Ser Gly Ser Gly Thr Asp Phe Thr Leu Thr Ile Ser Ser
Val Gln Ala Glu Asp Leu Ala Val Tyr Tyr Cys Lys Gln Ser
Tyr Asn Leu Trp Thr Phe Gly Gly Gly Thr Lys Leu Glu Ile
Lys Arg (SEQ ID NO:7)

FIG. 1

Met Gly Trp Val Trp Asn Leu Leu Phe Leu Met Ala Ala Ala
Gln Cys Ile Gln Ala Gln Ile Gln Leu Val Gln Ser Gly Pro
Glu Leu Lys Lys Pro Gly Glu Thr Val Lys Ile Ser Cys Lys
Ala Ser Gly Tyr Thr Phe Thr Asp Tyr Pro Leu His Trp Val
Lys Gln Ala Pro Gly Lys Gly Leu Gln Trp Met Ala Trp Ile
Asn Thr Glu Thr Gly Glu Pro Thr Tyr Ala Asp Asp Phe Thr
Gly Arg Phe Ala Phe Ser Leu Glu Thr Ser Ala Ser Thr Ala
Tyr Leu Gln Ile Asn Asn Leu Lys Asn Glu Asp Thr Ala Thr
Tyr Phe Cys Val Arg Gly Tyr Tyr Tyr Tyr Trp Gly Gln Gly
Thr Thr Leu Ser Val Ser Ser (SEQ ID NO:8)

FIG. 2

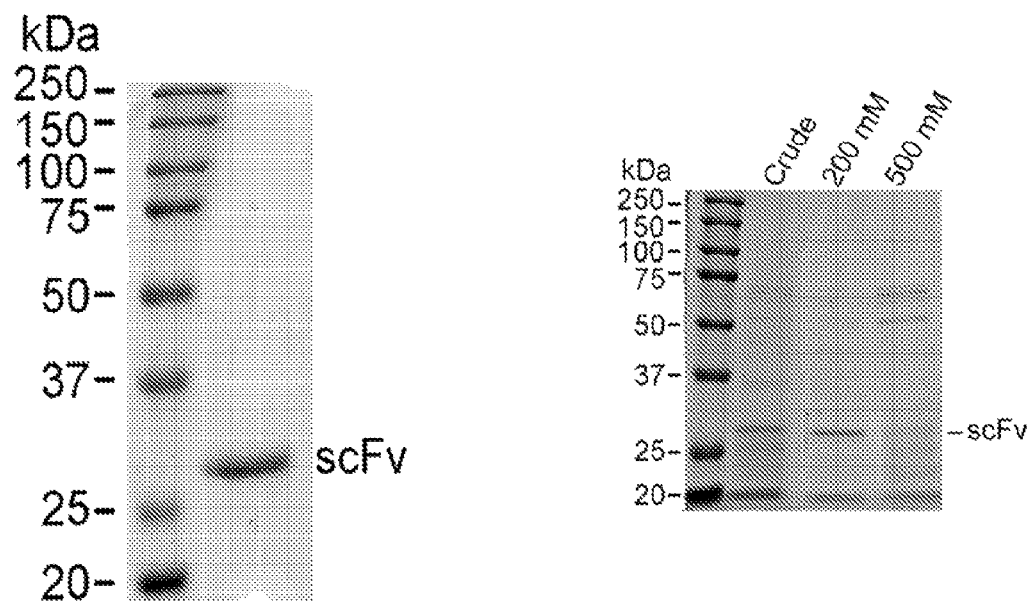
FIG. 5B
FIG. 5A
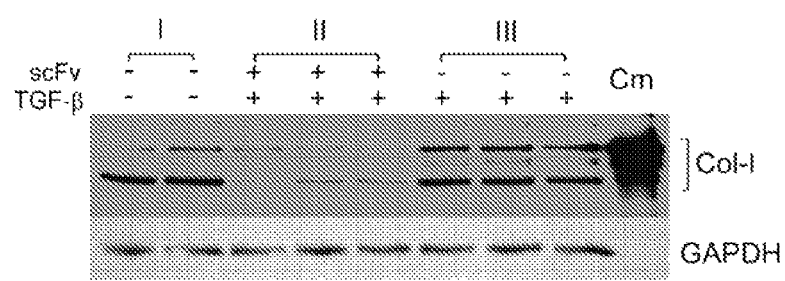
FIG. 8

FIG. 9A

|AgeI
cacgAccGGTCTAGAGCTCTAGGCTCTGAGAAGCTTGTCGACGAATTCAGATACTAGTGGACATGGTTCTCATGTTACTGCTGTCTATGGGTATCTGGT
                                                          Signal-Peptide
                                                    M  V  L  M  L  L  L  W  V  S  G ACCTGTGGGGACATTGTGATGTCACAGTCTCCATCCTCCCTGGCTGTGTCAGCAGGAGAGAAGGTCACTATGAGCTGCAAATCCAGTCAGAGTCTGCTCA
                              Signa...tide    mouse VL
T  C  G  D  I  V  M  S  Q  S  P  S  S  L  A  V  S  A  G  E  K  V  T  M  S  C  K  S  S  Q  S  L  L ACAGTAGAAACCCGAAAGAATAACTTGGCTTGGTACCAGCAGAAACCAGGGCAGTCTCCTAAACTGCTGATCTACTGGGCATCCACTAGGGAATCTGGGGT
                                                          mouse VL
N  S  R  T  R  K  N  N  L  A  W  Y  Q  Q  K  P  G  Q  S  P  K  L  L  I  Y  W  A  S  T  R  E  S  G  V CCCTGATCGCTTCACAGGCAGTGGATCTGGGACAGATTTCACTCTCACCATCAGCAGTGTGCAGGCTGAAGACCTGGCAGTTTATTACTGCAAGCAATCT
                                                          mouse VL
P  D  R  F  T  G  S  G  S  G  T  D  F  T  L  T  I  S  S  V  Q  A  E  D  L  A  V  Y  Y  C  K  Q  S

|BsiWI
TATAATCTGTGGACGTTCGGTGGAGGCACCAAGCTGGAAATCAAACGTACGGATGCTGC
            mouse VL
Y  N  L  W  T  F  G  G  G  T  K  L  E  I  K  R

FIG. 13

ENGINEERED ANTIBODY FOR INHIBITION OF FIBROSIS

REFERENCE TO GOVERNMENT GRANT

The benefit of the filing date of U.S. Provisional Patent Application No. 61/636,073, filed Apr. 20, 2012, is hereby claimed. The entire disclosures of the aforesaid application are incorporated herein by reference.

REFERENCE TO GOVERNMENT GRANT

The invention was made with government support under grant 5RO1 AR048544-05 and IR21AR061118-01 awarded by the National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on Feb. 25, 2013, is named 37075_0269_00_WO_SL.txt and is 30,011 bytes in size.

FIELD OF THE INVENTION

The invention relates to engineered antibodies for the treatment of fibrotic disorders.

BACKGROUND OF THE INVENTION

Collagen I, the most abundant structural protein of connective tissue such as skin, bone and tendon, is first synthesized as a precursor molecule, procollagen. Formation of collagen fibrils is initiated by enzymatic processing of procollagen to expose telopeptides, which engage in site-specific intermolecular interactions to drive collage self assembly. In vivo, collagen fibrils are stabilized by the covalent cross-links formed between fibril-incorporated collagen molecules. Self assembly of collagen molecules results in collagen fibrils, the main component of fibrotic lesions, particularly scarring.

Collagen/collagen binding is mediated through the interaction of the C-terminal $\alpha 1(I)$ and $\alpha 2(I)$ telopeptides of one collagen molecule, and the Triple-helical Telopeptide-Binding Region (T-TBR) of another binding partner. The T-TBR is located within an $\alpha 1(I)$ chain in the region flanked by resides 776 and 796 (Prockop, et al. (1998) *J Biol Chem.* 273, 15598-15604).

Fibrosis is the formation of excess fibrous connective tissue in an organ or tissue in a reparative or reactive process. Types of fibrosis include, for example, pulmonary fibrosis (lungs), idiopathic pulmonary fibrosis (where the cause is unknown), cirrhosis (liver), endomyocardial fibrosis (heart), mediastinal fibrosis (soft tissue of the mediastinum), myelofibrosis (bone marrow), retroperitoneal fibrosis (soft tissue of the retroperitoneum), progressive massive fibrosis (lungs), nephrogenic systemic fibrosis (skin), Crohn's Disease intestine, keloid (skin), myocardial infarction (heart), scleroderma/systemic sclerosis (skin, lungs), arthrofibrosis (knee, shoulder, other joints) and some forms of adhesive capsulitis (shoulder).

Although the fibrotic changes seen in excessive scarring may be triggered in many ways, such as trauma, accidental injury or surgical procedures, most of them are developed through fundamentally similar pathways that, in the end, lead to altering a number of functions of involved tissues. For instance, after surgery in the abdomen, the formation of excessive scar tissue around abdominal organs often interferes with their functionality. After plastic surgery to the face, the formation of excessive scar tissue frequently compromises the benefits of the surgery. Excessive scar formation also presents a major complication in the eye after glaucoma surgery performed to maintain a lamellar channel from the subconjunctival space to the anterior chamber. Frequently, however, the excessive scar formation closes this pressure-reducing channel, thereby forcing the intraocular pressure to rise (Addicks, et al. (1983) *Arch Ophthalmol.* 101, 795-798). Yet another significant problem with excessive formation of fibrous deposits is the foreign body response to medical devices and materials implanted in the human body (Anderson, et al. (2008) *Semin Immunol.* 20, 86-100). Moreover, excessive scarring of the vocal folds may severely alter their ability to vibrate, thereby causing a number of voice disorders (Lim, et al. (2006) *Ann Otol Rhinol Laryngol.* 115, 921-929). Another medical problem of localized fibrosis is the formation of keloids, excessive scars for which there are no successful treatment methods. This particular scarring is an ongoing and rising problem; as keloids are more common in Americans of African and Asian descent, it is expected that in the near future the number of keloid cases in the USA will increase due to the foreseen rise in the percentage of these ethnic groups (Taylor, et al. (2002) *J Am Acad Dermatol.* 46, S41-62).

To date, no effective therapeutics for excessive fibrosis are available. What is needed are therapeutics and therapeutic methods that can prevent the excessive deposition of collagen fibrils that is characteristic of fibrotic processes, and to reduce localized and systemic fibrotic lesions.

SUMMARY OF THE INVENTION

A chimeric, humanized or single-chain antibody is provided. The antibody comprises a light chain variable region comprising complementarity determining regions comprising the amino acid sequences SEQ ID NO:1, SEQ ID NO:2 and SEQ ID NO:3, and a heavy chain variable region comprising the complementarity determining regions comprising the amino acid sequences SEQ ID NO:4, SEQ ID NO:5 and SEQ ID NO:6. Also provided are fragments of said chimeric or humanized antibodies. The antibody or antibody fragment is capable of binding the C-terminal telopeptide of the $\alpha 2(I)$ chain of human collagen I.

In one embodiment, the antibody or antibody fragment is a chimeric antibody or chimeric antibody fragment. In one embodiment, the chimeric antibody comprises an antibody light chain comprising a light variable region having the amino acid sequence SEQ ID NO:10, and an antibody heavy chain comprising a heavy chain variable region having the amino acid sequence SEQ ID NO:11. In another embodiment, a fragment of said chimeric antibody is provided, which antibody fragment binds the C-terminal telopeptide of the $\alpha 2(I)$ chain of human collagen.

In embodiments of the chimeric antibody, the antibody light chain comprises a human antibody light chain constant region, and the antibody heavy chain comprises a human antibody heavy chain constant region. In another embodiment, a fragment of said chimeric antibody is provided, which antibody fragment binds the C-terminal telopeptide of the $\alpha 2(I)$ chain of human collagen. In some embodiments, the constant region comprises an IgG constant region.

In another embodiment, the antibody or antibody fragment is a humanized antibody or fragment of a humanized antibody, which fragment binds the C-terminal telopeptide of the α2(I) chain of human collagen. In some embodiments, the humanized antibody or antibody fragment comprises a human antibody framework region and/or a human antibody constant region. In some embodiment, the constant region comprises an IgG constant region. Also provided are fragment of said humanized antibody which bind the C-terminal telopeptide of the α2(I) chain of human collagen.

In other embodiments, the antibody is a single chain antibody. In one embodiment, the single chain antibody comprises a light chain variable region having the amino acid sequence shown in SEQ ID NO:9, SEQ ID NO:10 or SEQ ID NO:26, and a heavy chain variable region having the amino acid sequence shown in SEQ ID NO:11.

In certain embodiments, the single chain antibody comprises a linker comprising a sequence of amino acids that links the light chain variable region and the heavy chain variable region.

In some embodiments, the linker connects the carboxy terminus of the light chain variable region to the amino terminus of the heavy chain variable region. In other embodiments, the linker connects the carboxy terminus of the heavy chain variable region to the amino terminus of the light chain variable region.

In some embodiments, the linker may comprise the amino acid sequence Gly-Gly-Ser, or the amino acid sequence Gly-Gly-Gly-Gly-Ser (SEQ ID NO:29). In some embodiments, the linker comprises from two to twelve repeats of the amino acid sequence Gly-Gly-Ser or from two to twelve repeats of the amino acid sequence Gly-Gly-Gly-Gly-Ser (SEQ ID NO:29). In some embodiments, the aforesaid linker connects the carboxy terminus of the light chain variable region to the amino terminus of the heavy chain variable region. In other embodiments, the aforesaid linker connects the carboxy terminus of the heavy chain variable region to the amino terminus of the light chain variable region.

In an embodiment, the single chain antibody comprises the amino acid sequence shown in SEQ ID NO:12. In another embodiment, the single chain antibody comprises the amino acid sequence shown in SEQ ID NO:16.

Provided is a polynucleotide for expressing a chimeric antibody light chain, said polynucleotide comprising a first segment encoding an antibody light chain variable region having the amino acid sequence SEQ ID NO:10 and a second segment encoding a human antibody light chain constant region. In one embodiment, of the aforesaid polynucleotide, the first segment comprises the nucleotide sequence SEQ ID NO:22.

Provided is a polynucleotide for expressing a chimeric antibody heavy chain, said polynucleotide comprising a first segment encoding an antibody heavy chain variable region having the amino acid sequence SEQ ID NO:11 and a second segment encoding a human antibody heavy chain constant region. In one embodiment of the aforesaid polynucleotide, the first segment comprises the nucleotide sequence SEQ ID NO:23.

Provided is a polynucleotide for expressing a single chain antibody comprising a first segment encoding an antibody light chain variable region having the amino acid sequence shown in SEQ ID NO:9, SEQ ID NO:10 or SEQ ID NO:26, and a second segment encoding an antibody heavy chain variable region comprising the amino acid sequence shown in SEQ ID NO:11. In certain embodiments, the polynucleotide comprises a linker segment between said first and second segments. The linker segment encodes a linker comprising one or more amino acids. In certain embodiments, the linker segment encodes a linker comprising from two to twelve repeats of the amino acid sequence Gly-Gly-Ser, or from two to twelve repeats of the amino acid sequence Gly-Gly-Gly-Gly-Ser (SEQ ID NO:29). In embodiments, the first DNA segment comprises the nucleotide sequence SEQ ID NO:22, SEQ ID NO:27 or SEQ ID NO:28, and the second DNA segment comprises the nucleotide sequence SEQ ID NO:23.

In an embodiment, the polynucleotide for expressing a single chain antibody encodes a single chain antibody comprising the amino acid sequence SEQ ID NO:12. In an embodiment, the aforesaid polynucleotide comprises the nucleotides sequence SEQ ID NO:13.

In an embodiment, the polynucleotide for expressing a single chain antibody encodes a single chain antibody comprising the amino acid sequence SEQ ID NO:16. In an embodiment, the aforesaid polynucleotide comprises the nucleotide sequence SEQ ID NO:17.

Also provided are pharmaceutical compositions comprising the aforementioned chimeric, humanized or single-chain antibody, or fragment of a chimeric or humanized antibody, and a pharmaceutically acceptable carrier.

Also provided is a method of treating a disease or disorder associated with excessive collagen fibril formation in a subject, comprising administering to the subject an effective amount of the aforesaid antibody or antibody fragment. In one embodiment, the disease or disorder comprises scar formation. In some embodiments, the disease or disorder comprises fibrosis. Non-limiting examples of such fibroses include: pulmonary fibrosis, idiopathic pulmonary fibrosis, cirrhosis, endomyocardial fibrosis, mediastinal fibrosis, myelofibrosis, retroperitoneal fibrosis, progressive massive fibrosis, nephrogenic systemic fibrosis, Crohn's Disease, keloid formation, myocardial infarction, scleroderma/systemic sclerosis, arthrofibrosis, and adhesive capsulitis.

In certain embodiments of the method of treatment, the fibrosis results from a surgical procedure, e.g., abdominal surgery, plastic surgery, glaucoma surgery or surgery for implantation of a medical implant or device.

In another embodiment, the aforesaid chimeric, humanized or single-chain antibody, or fragment of a chimeric or humanized antibody is provided for use in medicine. In another embodiment, the aforesaid chimeric, humanized or single-chain antibody, or fragment of a chimeric or humanized antibody is for treating a disease or disorder associated with excessive collagen fibril formation in a subject. In another embodiment, the aforesaid chimeric, humanized or single-chain antibody, or fragment of a chimeric or humanized antibody is used for the preparation of a medicament for treating a disease or disorder associated with excessive collagen fibril formation in a subject.

BRIEF DESCRIPTION OF THE FIGURES

FIG. 1 shows the amino acid sequence (SEQ ID NO:7) of the light chain variable region of an engineered antibody of the invention. The complementarity determining regions (CDRs) are double-underlined. The first fifteen amino acids in FIG. 1 comprise a signal sequence. The signal sequenced is single-underlined.

FIG. 2 shows the amino acid sequence (SEQ ID NO:8) of the heavy chain variable region of an engineered antibody of the invention. The complementarity determining regions are double-underlined. The first nineteen amino acids in FIG. 2 comprise a signal sequence. The signal sequenced is single-underlined.

FIG. 5A shows an electrophoretic assay of a refolded scFv of the invention expressed in bacteria purified with anti-FLAG antibody. Electrophoretic migration of the purified single chain antibody indicates the predicted mass.

FIG. 5B shows an electrophoretic assay of the refolded single chain antibody expressed in bacteria and purified by ion exchange chromatography. The fraction including the scFv was eluted with 200 mM NaCl, while contaminating proteins were eluted with 500 mM NaCl.

FIG. 8 shows the inhibition of collagen fibril deposition in cultures of keloid-derived human fibroblasts by the scFv: (I) non treated, (II) treated with tissue growth factor β (TGF-β) and single chain antibody, and (III) treated only with TGF-β. Cell layers consisting of collagen-rich extracellular matrix and cells were collected and analyzed for the presence of collagen I (Col-I), a main constituent of collagen fibrils. An equal number of cells in the analyzed groups is indicated by comparable amounts of GAPDH. The analyzed groups and the collagen I marker (Cm) are indicated.

FIGS. 9A-9C show the DNA coding sequence (upper sequence, which is SEQ ID NO:19), the DNA non-coding sequence (middle sequence, which is SEQ ID NO:30), and amino acid (SEQ ID NO:18) sequences of the construct designated A_L_K, for the expression of an scFv in yeast. Restriction sites utilized in the cloning strategy are indicated.

FIG. 13 shows the DNA (SEQ ID NO:21) and amino acid (SEQ ID NO:7) sequences of a construct encoding a mouse light chain variable region ($mV_L$), for the preparation of a plasmid for expressing a chimeric antibody heavy chain consisting of the $mV_L$ and the constant region of a human κ chain ($mV_H$-hκ). Restriction sites utilized in the cloning strategy are indicated.

DEFINITIONS

Figure 3:
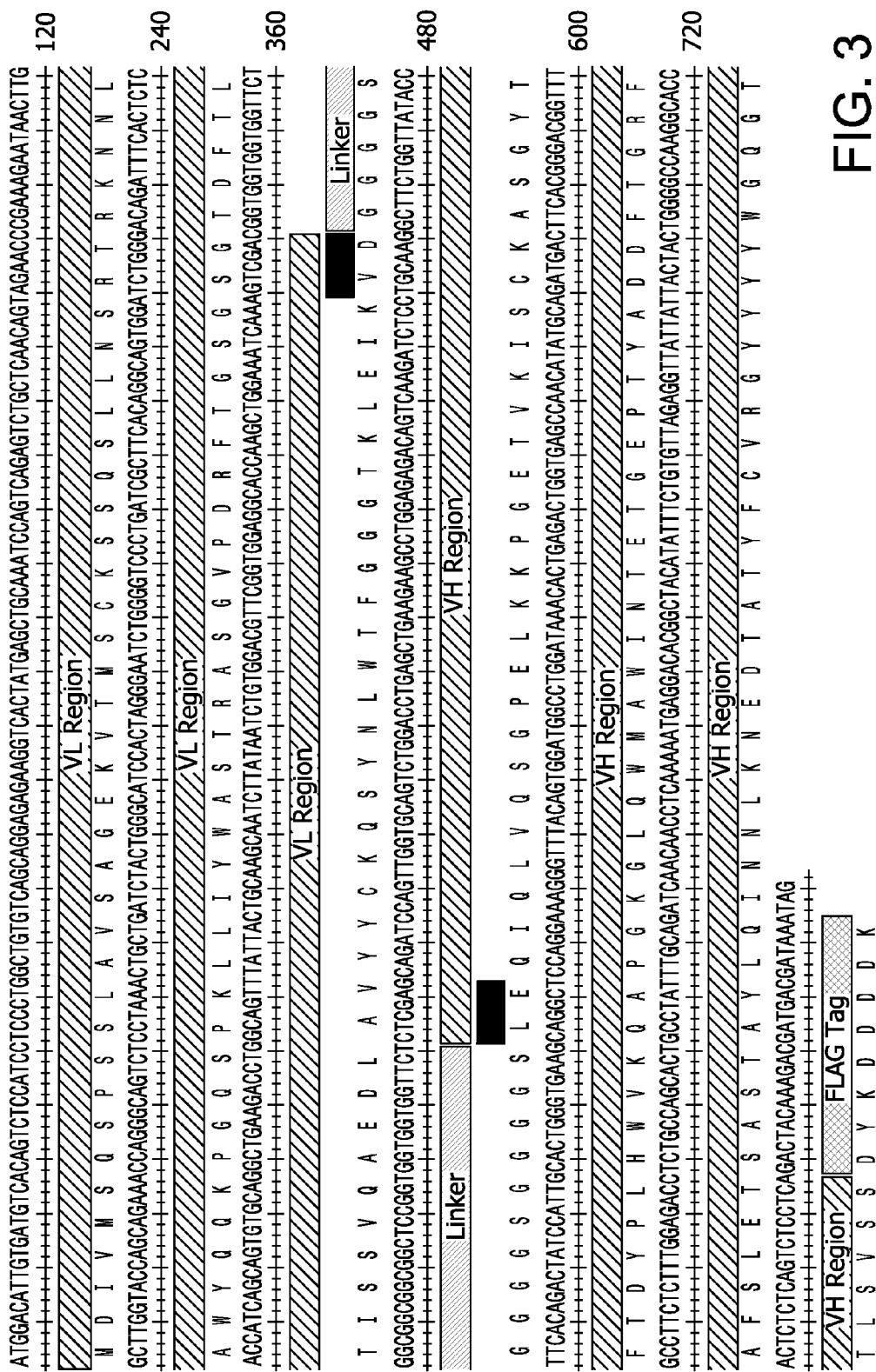
FIG. 3 shows the DNA (SEQ ID NO:15) and amino acid (SEQ ID NO:14) sequences of an scFv for bacterial expression. The sequences of the $V_H$ and $V_L$ regions as well as that of the linker are indicated. The black boxes indicate insertions made during the cloning process. A FLAG-tag is also indicated.

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

The term "about" will be understood by persons of ordinary skill in the art and will vary to some extent depending on the context in which it is used. As used herein, "about" is meant to encompass variations of ±20% or ±10%, more preferably ±5%, even more preferably ±1%, and still more preferably ±0.1%.

Unless otherwise specified herein, the terms "antibody" and "antibodies" broadly encompass naturally-occurring forms of antibodies (e.g., IgG, IgA, IgM, IgE) and recombinant antibodies as well as derivatives have at least an antigenic binding site. Antibody derivatives may comprise a protein or chemical moiety conjugated to an antibody.

By "chimeric antibody" is meant an antibody molecule in which different portions are derived from different animal species, such as those having a variable region derived from a murine antibody and a human immunoglobulin constant region. Typically, a chimeric antibody is composed of a variable region comprising light and heavy chain variable regions, and a constant region derived or obtained from a human antibody.

A "humanized antibody" refers to an antibody in which the complementarity defining regions (CDRs) of an antibody of a non-human mammal, e.g., mouse, are grafted to a human antibody. The variable domain of each of an antibody heavy chain and light chain comprise three CDRs; the intervening sequence segments are "framework segments". Each variable domain is composed of four framework segments. In a humanized antibody, the framework segments are typically of human origin.

A "single chain antibody", also known as a "single-chain variable fragment" (scFv) is a fusion protein of the variable regions of the heavy and light chains of an immunoglobulin, wherein the regions are optionally connected by a linker. As used herein, "single chain antibody" or "single-chain variable fragment" includes such fusion proteins, and also multimers (linear or branched) formed of such fusion proteins.

A "polynucleotide" as utilized in the practice of the present invention may include any polymer or oligomer of pyrimidine and purine bases, preferably cytosine, thymine, and uracil, and adenine and guanine, respectively. The polynucleotide may comprise any deoxyribonucleotide, ribonucleotide or peptide nucleic acid component, and any chemical variants thereof, such as methylated, hydroxymethylated or glucosylated forms of these bases, and the like. The polynucleotide may comprise DNA or RNA, or a mixture thereof, and may exist permanently or transitionally in single-stranded or double-stranded form, including homoduplex, heteroduplex, and hybrid states.

As used herein, the term "subject" or "patient" refers to any animal (e.g., a mammal), including, but not limited to humans, non-human primates, rodents, and the like. Typically, the terms "subject" and "patient" are used interchangeably herein in reference to a human subject.

The term "treating" as used herein, unless otherwise indicated, means reversing, alleviating, inhibiting the progress of, or preventing, either partially or completely, an indicated disease or disorder. The term "treatment" as used herein, unless otherwise indicated, refers to the act of treating. The term "treating" does not necessarily mean that the disease or disorder will, in fact, be eliminated.

The term "therapeutically effective amount" or "effective amount" means the amount of a subject compound or combination that will elicit the biological or medical response of a tissue, system, animal or human that is being sought.

As envisioned in the present invention with respect to the disclosed compositions of matter and methods, in one aspect the embodiments of the invention comprise the components and/or steps disclosed herein. In another aspect, the embodiments of the invention consist essentially of the components and/or steps disclosed herein. In yet another aspect, the embodiments of the invention consist of the components and/or steps disclosed herein.

DETAILED DESCRIPTION OF THE INVENTION

Engineered antibodies are provided that bind to the C-terminal telopeptides of the α2-chain of collagen. The engineered antibodies inhibit the formation of collagen fibrils. Free collagen molecules that do not incorporate into fibrils are readily accessible for degradation by enzymes present in the extracellular space (Prockop and Fertala, *J. Biol. Chem.* 273:15598-15604 (1988); Chang et al., *Diabetes* 29:778-781 (1980)). The engineered antibodies comprise a heavy chain variable region comprising the three complementarity determining regions having the amino acid sequences shown in SEQ ID NO:1, SEQ ID NO:2 and SEQ ID NO:3, and a light chain variable region comprising the three complementarity determining regions having the amino acid sequences shown in SEQ ID NO:4, SEQ ID NO:5 and SEQ ID NO:6. The engineered antibodies are capable of binding the C-terminal telopeptide of the α2(I) chain of human collagen I.

In one embodiment, the engineered antibody is a chimeric antibody comprising the mouse light chain variable region ($mV_L$) having the amino acid sequence of SEQ ID NO:10, and the mouse heavy chain variable region ($mV_H$) having the amino acid sequence of SEQ ID NO:11. The mouse light chain variable region and mouse heavy chain variable regions, with predicted signal peptides, are shown in FIGS. 1 and 2, respectively. The $mV_L$ and $mV_H$ complementarity determining regions are shown by double underlining in FIG. 1 and FIG. 2. The first fifteen amino acids in FIG. 1 (indicated by single underlining) comprise the signal sequence for the $mV_L$. The first nineteen amino acids in FIG. 2 (indicated by single underlining) comprise the signal sequence for the $mV_H$.

Using the sequences encoding the above light and heavy chain variable regions, chimeric antibodies may be produced by any of the well-known techniques for production of chimeric antibodies (Morrison et al., 1984, *Proc. Natl. Acad. Sci.*, 81:6851-5; Neuberger et al., 1984, *Nature*, 312:604-8; Takeda et al., 1985, *Nature*, 314:452-4). Accordingly, a DNA molecule encoding the light chain variable region SEQ ID NO:10, e.g., the DNA molecule having the nucleotide sequence of SEQ ID NO:22, is prepared. The DNA molecule may further encode a signal sequence for the light chain variable region, such as the fifteen amino acid signal sequence shown in FIG. 1 by single underlining. SEQ ID NO:7 is the amino acid sequence of the polypeptide comprising the signal sequence and light chain variable region shown in FIG. 1. SEQ ID NO:7 may be encoded by, for example, the nucleotide sequence of SEQ ID NO:24.

A DNA molecule encoding the heavy chain variable region SEQ ID NO:11, e.g., the DNA molecule having the nucleotide sequence of SEQ ID NO:23, is prepared. The DNA molecule may further encode a signal sequence for the heavy chain variable region, such as the nineteen amino acid signal sequence shown in FIG. 2 by single underlining. SEQ ID NO:8 is the amino acid sequence of the polypeptide comprising the signal sequence and heavy chain variable region shown in FIG. 2. SEQ ID NO:8 may be encoded by, for example, the nucleotide sequence of SEQ ID NO:25.

The DNA molecules encoding the light and heavy chain variable regions are then ligated into vector DNA and expressed using, for example, any of the available ligation kits to construct a recombinant vector. See e.g., J. Sambrook et, *Molecular Cloning*, Cold Spring Harbor Laboratory Press, 1989.

In one embodiment, a chimeric antibody may be prepared by ligating a mouse leader sequence and a variable region sequence present in a cloned mouse cDNA to a sequence coding for a human antibody constant region already present in an expression vector of a mammalian cell. Alternatively, a mouse leader sequence and a variable region sequence present in a cloned cDNA are ligated to a sequence coding for a human antibody constant region followed by ligation to a mammalian cell expression vector. The mouse leader sequence may comprise, for example, the signal sequences shown in FIG. 1 or FIG. 2.

The polypeptide comprising human antibody constant region can comprise any of the heavy or light chain constant regions of human antibodies, including, for example, γ1, γ2, γ3 or γ4 for heavy chains, and κ for light chains.

To prepare a chimeric antibody, two expression vectors are constructed. A first expression vector contains DNAs coding for the light chain variable region and human light chain constant region under the control of an expression control element such as an enhancer/promoter system. A second expression vector contains DNAs coding for the heavy chain variable region and human heavy chain constant region under the control of an expression control element such as an enhancer/promoter system. Host cells such as mammalian cells (for example, COS cell) are cotransformed with these expression vectors. The transformed cells are cultivated in vitro or in vivo to produce a chimeric antibody, See, e.g. WO91/16928.

As an alternative, mouse leader sequence present in cloned cDNA and DNAs coding for mouse light chain variable region and human light chain constant regions, as well as a mouse leader sequence and DNAs coding for mouse heavy chain variable region and human heavy chain constant region, are introduced into a single expression vector (see, for example, WO94/11523). The single vector is used to transform a host cell. The transformed host is cultured in vivo or in vitro to produce a desired chimeric antibody.

The vector for the expression of the heavy chain of the chimeric antibody can be obtained by introducing cDNA comprising a nucleotide sequence coding for the mouse heavy chain variable region into a suitable expression vector containing genomic DNA comprising a nucleotide sequence coding for the heavy chain constant region of human antibody, or cDNA coding for the heavy chain constant region. As indicated above, the heavy chain constant region may comprise, for example, γ1, γ2, γ3 or γ4.

Expression vectors comprising genomic DNA coding for a heavy chain constant region include, for example, HEF-PMh-g gamma 1 (WO92/19759) and DHER-INCREMENT E-RVh-PM1-f (WO92/19759). Alternatively, a human constant region library can be prepared using cDNA from human peripheral blood mononuclear cells, as described by Liu. et al., *Proc. Natl. Acad. Sci. USA*, 84:3439-43 (1987) or Reff et al., *Blood* 83(2): 435-45 (1994), for example.

The cDNA coding for the mouse heavy chain variable region of SEQ ID NO:11 (e.g., the nucleotide sequence SEQ ID NO:23, which does not contain a signal sequence segment; or the nucleotide sequence of SEQ ID NO:25, which contains a signal sequence) is treated with suitable restriction enzyme(s) and inserted into genomic DNA coding for a heavy chain constant region, to construct a chimeric heavy chain expression vector containing the genome DNA coding for the heavy chain constant region. Insertion is by ligation of the cDNA encoding the heavy chain constant region, and insertion into an expression vector such as pQCXIH (Clontech), to construct an expression vector containing the complete cDNA encoding the complete chimeric heavy chain. Alternatively, the cDNA encoding the mouse heavy chain variable region may be ligated into an appropriate commercially available cloning plasmid that expresses the constant region of a human heavy chain, e.g., pFUSE-CHIg-hG1 (InvivoGen, San Diego, Calif.).

In a similar fashion, a vector for the expression of the light chain of the chimeric antibody can be constructed by ligating a cDNA coding for the mouse light chain variable region (e.g., the nucleotide sequence SEQ ID NO:22, which does not contain a signal sequence; or the nucleotide sequence of SEQ ID NO:24, which contains a signal sequence) and a genomic DNA or cDNA coding for the light chain constant region of a human antibody, and introduction into a suitable expression vector. The light chain constant region includes, for example, κ or λ, chains. Any of the four known λ chain constant region isotypes may be utilized. Alternatively, the cDNA encoding the mouse light chain variable region may be ligated into an appropriate commercially available cloning plasmid that expresses the constant region of a human κ light chain, e.g., pFUSE2-CLIg-hκ (InvivoGen, San Diego, Calif.).

Figure 11:
FIG. 11 shows the DNA (SEQ ID NO:20) and amino acid (SEQ ID NO:8) sequences of a construct encoding a mouse heavy chain variable region ($mV_H$), for the preparation of a further construct for expressing a chimeric antibody heavy chain consisting of the $mV_H$ and the constant region of a human γ chain ($mV_H$-hγ). Restriction sites utilized in the cloning strategy are indicated.
Figure 12:
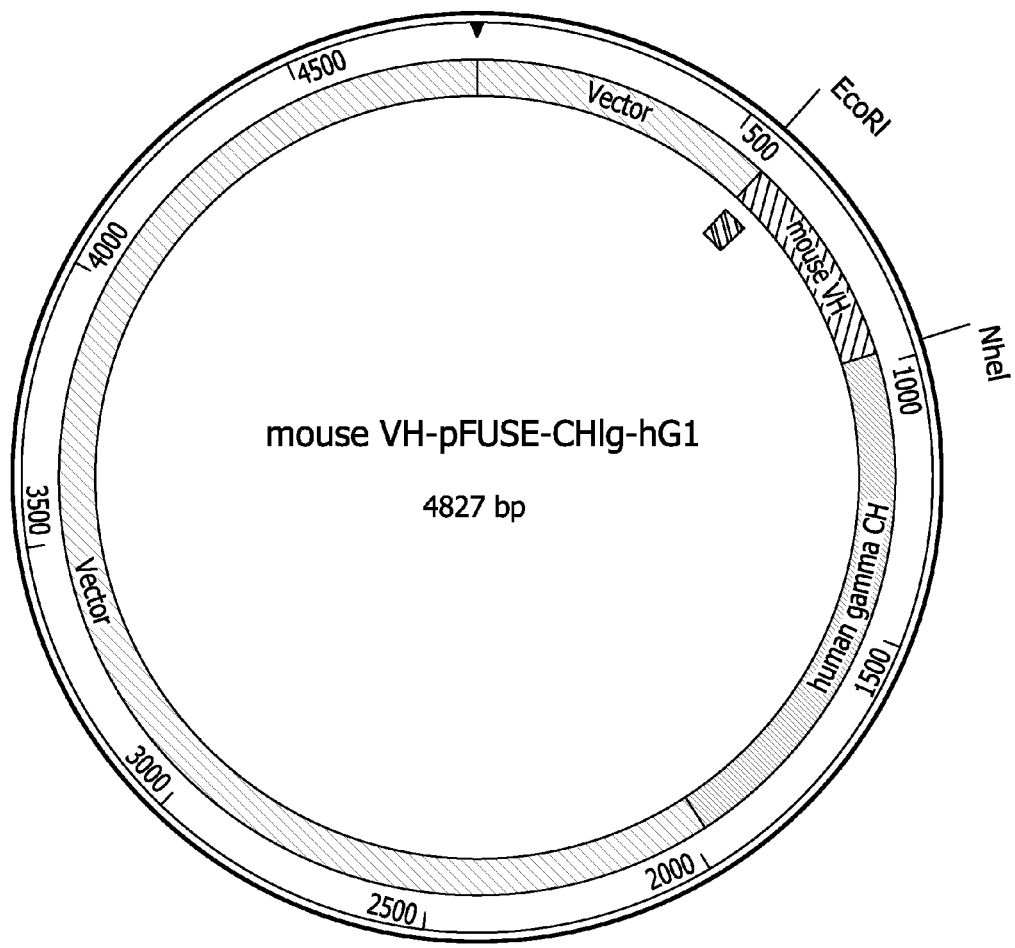
FIG. 12 is a schematic of a plasmid for expression of the $mV_H$-hγ, utilizing the $mV_H$ construct of FIG. 11. The $mV_H$ construct was cloned into the pFUSE-CHIg-hG1 plasmid as shown in FIG. 12 to express the $mV_H$-hγ. Restriction sites utilized in the cloning strategy are indicated.

FIG. 11 shows the DNA (SEQ ID NO:20) and amino acid (SEQ ID NO:8) sequences of a construct encoding a mouse heavy chain variable region ($mV_H$) containing a leader signal peptide, for the preparation of a further construct for expressing a chimeric antibody heavy chain consisting of the $mV_H$ and the constant region of a human γ chain ($mV_H$-hγ). FIG. 12 is a schematic of a plasmid for expression of the $mV_H$-hγ, utilizing the $mV_H$ construct of FIG. 11. The $mV_H$ construct was cloned into the pFUSE-CHIg-hG1 plasmid as shown in FIG. 12. Restriction sites utilized in the cloning strategy are indicated.

Figure 14:
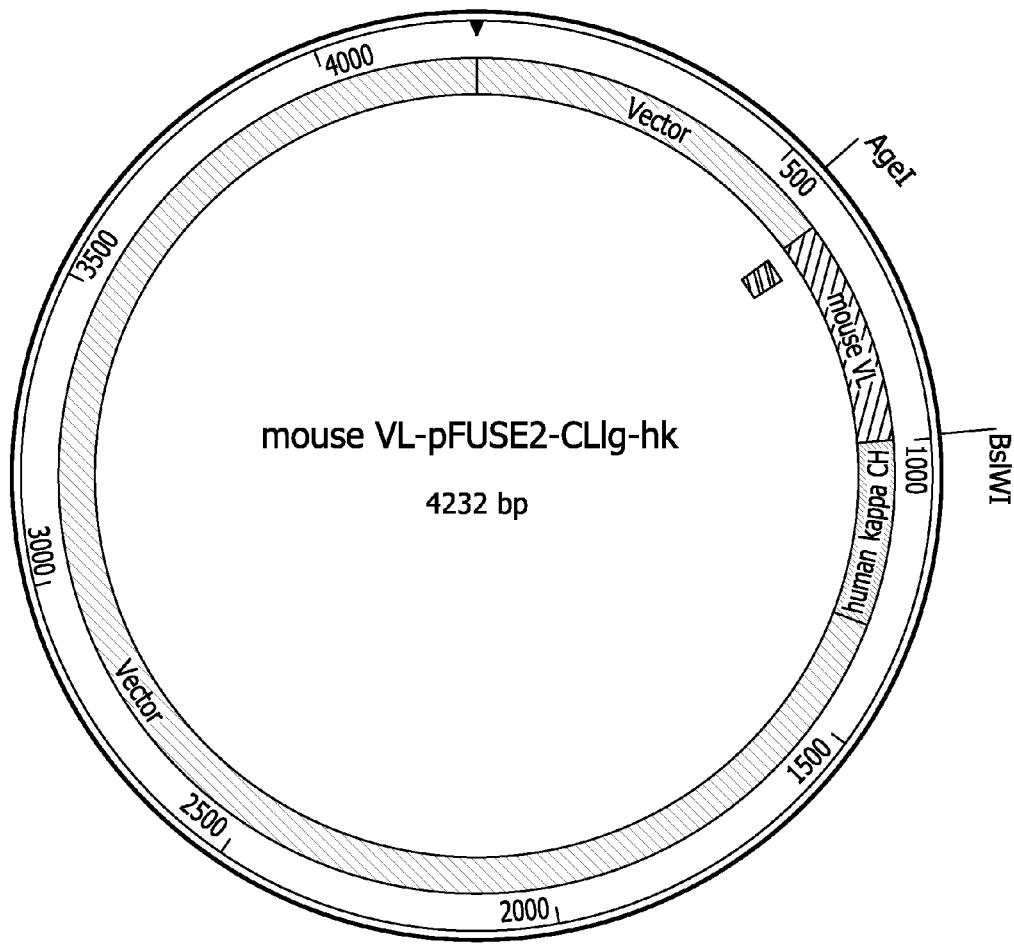
FIG. 14 is a schematic of a plasmid for expression of the chimeric $mV_L$-hκ utilizing the $mV_L$ construct of FIG. 13. The $mV_L$ construct was cloned into the pFUSE2-CLIg-hk plasmid as shown in FIG. 14 to express the $mV_H$-hκ. Restriction sites utilized in the cloning strategy are indicated.

FIG. 13 shows the DNA (SEQ ID NO:21) and amino acid (SEQ ID NO:7) sequences of a construct encoding a mouse light chain variable region ($mV_L$) containing a leader signal peptide, for the preparation of a plasmid for expressing a chimeric antibody heavy chain consisting of the $mV_L$ and the constant region of a human κ chain ($mV_L$-hκ). FIG. 14 is a schematic of a plasmid for expression of the chimeric $mV_L$-hκ, utilizing the $mV_L$ construct of FIG. 13. The $mV_L$ construct was cloned into the pFUSE2-CLIg-hκ plasmid as shown in FIG. 14. Restriction sites utilized in the cloning strategy are indicated.

In another embodiment, the engineered antibody is a humanized antibody. The humanized antibody comprises a human antibody framework region and advantageously further comprises a human antibody constant region. The six complementarity determining regions (CDRs) SEQ ID NOS:1-6 are grafted to a human antibody. The general genetic recombination procedure for producing humanized antibodies are described, for example, in EP 125023 and WO 96/02576. Accordingly, a DNA sequence is designed in which DNA encoding the aforementioned CDRs are ligated through framework regions. The DNA sequence is synthesized by a polymerase chain reaction method using oligonucleotide primers which are designed to have regions overlapping the terminal regions of the CDRs and the framework regions. The resultant DNA is ligated to DNA encoding the human antibody constant region, and the ligation product is integrated into an expression vector. The resultant recombinant expression vector is introduced into a host, thereby producing the humanized antibody. See, e.g., WO 96/02576.

The framework regions ligated through the CDRs are selected so that the CDRs can form a functional antigen binding site. If necessary, an amino acid(s) in the framework regions of the antibody variable region may be replaced so that the CDRs of the resulting humanized antibody can form an appropriate antigen binding site. See Sato et al., *Cancer Res.* 53:851-6 (1993).

The amino acid sequences of the framework regions are preferably selected to reflect a high homology to the framework sequences of a human antibody. In this regard, a comparison may be undertaken between the variable regions SEQ ID NO:10 and SEQ ID NO:11 and the variable regions of structurally elucidated human antibodies using, e.g., the Protein Data Bank. Other research tools that may consulted include the *Kabat Database of Sequences of Proteins of Immunological Interest*, www<<dot>>kabatdatabase <<dot>>com and the search tools included as part of that database; and Kabat, E. A. et al., (1991) *Sequences of Proteins of Immunological Interest*, 5$^{th}$ edition. U.S. Department of Health and Human Services.

A humanized antibody variable region is selected as a basis for the humanized antibody variable region. For example, the framework region of a human antibody variable region having a high homology, e.g., greater than about 80%, or greater than about 90%, or greater than about 95%, with the framework regions of SEQ ID NOS:10 and 11 (the non-CDR regions of SEQ ID NOS:10 and 11) is selected. A polypeptide comprising the framework regions of the humanized antibody and the CDRs of SEQ ID NOs:1-6 can be produced by "CDR-grafting", a PCR-based method utilizing a DNA fragment of a human antibody as a template. For an example of CDR grafting, see Kettleborough et al., *Protein Eng.* 4(7):773-783 (1991); "Antibody Humanization by CDR Grafting", *Methods of Molecular Biology*, 248(11): 135-159 (2004).

Humanized antibodies may be prepared, as exemplified in Jones et al., 1986 *Nature* 321:522-525, which describes replacing the complementarity-determining regions in a human antibody with those from a mouse. Also see Riechmann, 1988, *Nature* 332:323-327; Queen et al., 1989, *Proc. Nat. Acad. Sci. USA* 86:10029 (preparation of humanized antibody binding the interleukin 2 receptor); and Orlandi et al., 1989, *Proc. Natl. Acad. Sci. USA* 86:3833 (describing the cloning of immunoglobulin variable domains for expression by the polymerase chain reaction).

Any suitable expression system may be used to produce the chimeric or humanized antibody. For example, eukaryotic cells include animal cells such as established mammalian cell lines, fungal cells, and yeast cells; prokaryotic cells include bacterial cells such as *Escherichia coli*. Mammalian host cells are preferred. The expression system may incorporate conventional promoters useful for the expression in mammalian cells, e.g., the human cytomegalovirus (HCMV) immediate early promoter. Promoters for expression in mammalian cells may include virus promoters, such as those of retrovirus, polyoma virus, adenovirus and simian virus (SV) 40, and mammalian cell derived promoters, such as those of human polypeptide chain elongation factor-1 alpha (HEF-1 alpha).

The expression system may include a replication origin such as those derived from SV40, polyoma virus, adenovirus or bovine papilloma virus (BPV). The expression vector may comprise a gene for phosphotransferase APH(3') II or I (neo), thymidine kinase (TK), *E. coli* xanthine-guanine phosphoribosyltransferase (Ecogpt) or dihydrofolate reductase (DHFR) as a selective marker for increasing the gene copy number in a host cell system.

The expressed chimeric or humanized antibody is produced by culturing the thus-transformed host cells, and isolating and purifying the antibody from the cells according to well-known techniques. The concentration of the resulting purified antibody can be determined by, for example, enzyme-linked immunosorbent assay (ELISA). Antigen-binding activity can be confirmed by known methods antibody, techniques such as ELISA, enzyme immunoassay, radioimmunoassay or fluorescent assay.

Fragments of the chimeric or humanized antibody retaining antigen-binding activity may be prepared, e.g., Fab, F(ab')$_2$, and Fv fragments. Antibody fragments can be produced by cleaving the antibody with an enzyme (e.g., papain, pepsin) into antibody fragments, or by constructing a gene encoding the antibody fragment and inserting the gene into an expression vector and introducing the resultant recombinant expression vector into a suitable host cell, thereby expressing the antibody fragment (see, for example, Co et al., *J. Immunol.* 152:2968-76 (1994)).

In another embodiment, the engineered antibody is a single-chain antibody (SCA), also referred to herein as a single-chain variable fragment (scFv), comprising a light chain variable region comprising the complementarity determining regions (CDRs) having the amino acid sequences shown in SEQ ID NO:1, SEQ ID NO:2 and SEQ ID NO:3, and a heavy chain variable region comprising the complementarity determining regions having the amino acid sequences shown in SEQ ID NO:4, SEQ ID NO:5 and SEQ ID NO:6. The scFv can be produced by ligating a heavy chain variable region comprising the CDRs of SEQ ID NOS:4, 5 and 6 to a light chain variable region comprising the CDRs of SEQ ID NOS:1, 2 and 3 through a linker. The linker is preferably a peptide linker, i.e., the linker is composed of amino acid residues. The residues for the linker may be selected from naturally occurring amino acids, non-naturally occurring amino acids, and modified amino acids. The linker will typically connect the carboxy terminus of the heavy chain variable region to the amino terminus of said light chain variable region. The reverse is also possible, i.e., using the linker to connect the carboxy terminus of the light chain variable region to the amino terminus of the heavy chain variable region. The linker may comprise any number of amino acids. The linker may thus comprise, for example, 1, 2, 3, 4, 5, 6, 7, 8, 9, 10, 11, 12, 13, 14, 15, 16, 17, 18, 19, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, or more amino acids. In some embodiments, the linker may be composed of from 3 to 60 amino acid residues, from 3 to 40 amino acids, from 3 to 30 amino acids, from 3 to 24 amino acids, from 3 to 18 amino acids, or from 3 to 15 amino acids. The linker may comprise, for example, a repeating sub-sequence of 2, 3, 4, 5 or more amino acid residues, comprising 2, 3, 4, 5, 6, 7, 8, 9, 10, 11, 12 or more repeats of the sub-sequence.

In one embodiment, the linker comprises the amino acid sequence Gly-Ser, or repeats thereof. See, e.g., Huston, et al., *Methods in Enzymology,* 203:46-88 (1991). In another embodiment, the linker comprises the amino acid sequence Glu-Lys, or repeats thereof. See, e.g., Whitlow et al., *Protein Eng.,* 6:989 (1993)). In another embodiment, the linker comprises the amino acid sequence Gly-Gly-Ser, or repeats thereof. In another embodiment, the linker comprises the amino acid sequence Gly-Gly-Gly-Gly-Ser (SEQ ID NO:29), or repeats thereof. In certain specific embodiments, the linker contains from 2 to 12 repeats of Gly-Gly-Ser or Gly-Gly-Gly-Gly-Ser (SEQ ID NO:29).

An scFv of the invention having the amino acid sequence SEQ ID NO:14 is illustrated in FIG. 3. The scFv comprises from amino terminus to carboxy terminus, (i) an initial methionine residue, (ii) the $mV_L$ sequence SEQ ID NO:9, which comprises the parental $mV_L$ of SEQ ID NO:10 without the terminal Arg residue of SEQ ID NO:10, (iii) Val-Asp, (iv) a linker, (v) Leu-Glu, (vi) the $mV_H$ sequence SEQ ID NO.11, and (vii) a FLAG-Tag for affinity chromatography purification.

The antibody or antibody fragments of the invention may be utilized to bind to the C-terminal telopeptides of the α2-chain of collagen to inhibit the formation of collagen fibrils, and thereby prevent excessive deposition of collagen fibrils that is characteristic of fibrotic processes. The antibody or antibody fragments of the invention may thus be utilized to reduce localized and systemic fibrotic lesions, including but not limited to fibroses occurring in internal organs, the dermus or the eye.

Types of fibrosis that may be treated or prevented include, for example, pulmonary fibrosis, idiopathic pulmonary fibrosis, cirrhosis, endomyocardial fibrosis, mediastinal fibrosis, myelofibrosis, retroperitoneal fibrosis, progressive massive fibrosis, nephrogenic systemic fibrosis, Crohn's Disease, keloid formation, myocardial infarction, scleroderma/systemic sclerosis, arthrofibrosis, and adhesive capsulitis. The fibrotic lesion treated may be triggered by trauma, accidental injury or surgical procedures, among other causes. The antibody or antibody fragments of the invention may be administered, for example, after surgery in the abdomen to avoid the formation of excessive scar tissue around abdominal organs; after plastic surgery to the face to reduce scar formation; to the eye following glaucoma surgery performed to maintain a lamellar channel from the subconjunctival space to the anterior chamber, to prevent excessive scar formation that may function to closes the pressure-reducing channel and cause intraocular pressure to rise; and following implantation of medical devices and materials implanted in the human body, which would otherwise trigger a fibrotic response. In one embodiment, the antibody or antibody fragments are administered to teat or prevent the formation of keloids, Pharmaceutical compositions for use in accordance with the present invention can be formulated in conventional manner using one or more pharmaceutically acceptable carriers or excipients. The antibodies or fragments thereof can be formulated for administration in accordance with the route of administration. Formulations for injection can be presented in unit dosage form, e.g., in ampoules or in multi-dose containers, with an added preservative. The compositions can take such forms as suspensions, solutions, or emulsions in oily or aqueous vehicles, and can contain formulatory agents such as suspending, stabilizing and/or dispersing agents. Alternatively, the antibody can be in lyophilized powder form for constitution with a suitable vehicle, e.g., sterile pyrogen-free water, before use.

In some embodiments, the subject of treatment is human. In other embodiments, the subject is a veterinary subject.

Treatment may involve administration of one or more antibodies or antibody fragments of the invention, alone or with a pharmaceutically acceptable carrier. The active agent may be administered in combination with one or more other therapeutic, diagnostic or prophylactic agents. The administered composition may thus further comprise an additional agent selected from the group consisting of corticosteroids, antiinflammatories, immunosuppressants, antimetabolites, and immunomodulators, for example.

The pharmaceutically acceptable carrier may comprise any solvents, dispersion media, coatings, antibacterial and antifungal agents, isotonic and absorption enhancing or delaying agents, and the like that are physiologically compatible. Some examples of pharmaceutically acceptable carriers are water, saline, phosphate buffered saline, acetate buffer with sodium chloride, dextrose, glycerol, polyethylene glycol, ethanol and the like, as well as combinations thereof. In some cases, it will be preferable to include isotonic agents, for example, sugars, polyalcohols such as mannitol, sorbitol, or sodium chloride in the composition. Additional examples of pharmaceutically acceptable substances are surfactants, wetting agents or minor amounts of auxiliary substances such as wetting or emulsifying agents, preservatives or buffers, which enhance the shelf life or effectiveness of the antibody.

The compositions used in the practice of the invention may be in a variety of forms, for example, liquid, semi-solid and solid dosage forms, such as liquid solutions, dispersions or suspensions, tablets, pills, lyophilized cake, dry powders, liposomes and suppositories. The preferred form depends on the intended mode of administration and therapeutic application. In some embodiments, the antibody or antibody fragment may be administered by using a pump, enema, suppository, or indwelling reservoir or such like.

Therapeutic compositions typically must be sterile and stable under the conditions of manufacture and storage. The composition can be formulated as a solution, lyophilized cake, dry powder, microemulsion, dispersion, liposome, or other ordered structure suitable to high drug concentration. Sterile solutions can be prepared by incorporating the antibody or fragment in the required amount in an appropriate solvent with one or a combination of ingredients enumerated above, as required, followed by sterilization. In the case of sterile powders for the preparation of sterile solutions, the preferred methods of preparation are vacuum drying and freeze-drying that yields a powder of the active ingredient plus any additional desired ingredient from a previously sterile solution thereof. Generally, dispersions are prepared by incorporating the active compound into a sterile vehicle that contains a basic dispersion medium and the required other ingredients from those enumerated above. The desired characteristics of a solution can be maintained, for example, by the use of surfactants and the required particle size in the case of dispersion by the use of surfactants, phospholipids and polymers. Prolonged absorption of injectable compositions can be brought about by including in the composition an agent that delays absorption, for example, monostearate salts, polymeric materials, oils and gelatin.

In certain embodiments, the antibody or antibody fragment compositions of the invention may be prepared with a carrier that will protect the antibody against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems* (J. R. Robinson, ed., Marcel Dekker, Inc., New York (1978)).

The compositions of the invention may be administered parenterally. The term "parenteral" as used herein includes subcutaneous, intravenous, intramuscular, intra-articular, intra-synovial, intrasternal, intrathecal, intrahepatic, intralesional and intracranial injection or infusion techniques.

The compositions of the invention may be given orally, in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch.

The compositions of the invention may be administered topically. For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water. Topically-transdermal patches may also be used. For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

Topical or other localized administration is advantageously utilized at the site of a localized fibrosis, e.g., by localized injection. The location of the fibrosis may comprise, for example, a wound, particularly a wound edge.

The dosage of active agent may vary according to factors such as the disease state, age, sex, and weight of the individual, and the ability of the antibody or antibody portion to elicit a desired response in the individual. A therapeutically effective amount is also one in which any toxic or detrimental effects of the antibody or antibody portion are outweighed by the therapeutically beneficial effects. Detection and measurement of indicators of efficacy may be measured by a number of available diagnostic tools, including, for example, by physical examination including blood tests, pulmonary function tests, and chest X-rays; CT scan; bronchoscopy; bronchoalveolar lavage; lung biopsy and CT scan. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount may be less than the therapeutically effective amount.

Dosage regimens can be adjusted to provide the optimum desired response (e.g., a therapeutic or prophylactic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a pre-determined quantity of active compound calculated to produce the desired therapeutic effect in association with the required pharmaceutical carrier.

As a non-limiting example, an effective amount of an antibody or antibody fragment active agent is from about 0.025 to about 50 mg/kg, or from about 0.1 to about 50 mg/kg, or from about 0.1-25 mg/kg, or from about 0.1 to about 10 mg/kg, or from about 0.1 to about 3 mg/kg. Dosage may vary with the type and severity of the condition to be alleviated. For any particular treatment subject, specific dosage regimens may be adjusted over time according to the individual need and the professional judgment of the person administering or supervising the administration of the compositions, and that dosage ranges set forth herein are exemplary only and are not intended to limit the scope or practice of the claimed composition.

The practice of the invention is illustrated by the following non-limiting example. The invention should not be construed to be limited solely to the compositions and methods described herein, but should be construed to include other compositions and methods as well. One of skill in the art will know that other compositions and methods are available to perform the procedures described herein.

EXAMPLES

Example 1: Single-Chain Antibody by Bacterial Expression

A construct for preparing a single chain antibody, also referred to herein as a single-chain variable fragment (scFv), was prepared containing DNA sequences encoding the light chain variable region of SEQ ID NO:7 and the heavy chain variable region of SEQ ID NO:8. The DNA sequences were obtained by PCR from a hybridoma expressing an IgA class antibody to collagen α2-chain (Chung et al., *J Biol. Chem.* 283(38):25879-25886 (2008)). Total RNA was prepared from hybridoma cells with the use of an RNA-isolation kit according to the manufacturer's protocol (QIAGEN). PCR products spanning the $V_H$ of the α and the $V_L$ of the κ chains were cloned into the pETBlue-1 Blunt vector and sequenced.

A. Bacterial Expression System

For the bacterial expression of the scFv, a construct was created in which the $V_L$ region was connected with the $V_H$ region via a 15 amino acid linker comprising three repeats of the Gly-Gly-Gly-Gly-Ser (SEQ ID NO:29) motif. A DNA sequence encoding a FLAG tag was fused to the 3' end of the construct to facilitate downstream purification of the recombinant scFv (FIG. 3). Minor additions to the original amino acid sequences of the $V_L$ (SEQ ID NO:10) and $V_H$ (SEQ ID NO:11) regions were created as a consequence of the cloning process (FIG. 3). Moreover, the native signal peptides shown in FIGS. 1 and 2 (single underlining) were omitted in the scFv construct. The constructs were thus arranged to provide a scFv comprising, from N-terminus to C-terminus, light chain variable region-linker-heavy chain variable region, where the linker connected the N-terminus of the heavy chain to the C-terminus of the light chain. More specifically, the scFv comprised, from amino terminus to carboxy terminus, (i) an initial methionine residue, (ii) the $mV_L$ sequence SEQ ID NO:9, which comprises the parental $mV_L$ of SEQ ID NO:10 without the terminal Arg residue of SEQ ID NO:10, (iii) Val-Asp, (iv) a linker, (v) Leu-Glu, (vi) the $mV_H$ sequence SEQ ID NO.11, and (vii) a FLAG-Tag. The fidelity of the construct was confirmed by DNA sequencing.

Figure 4:
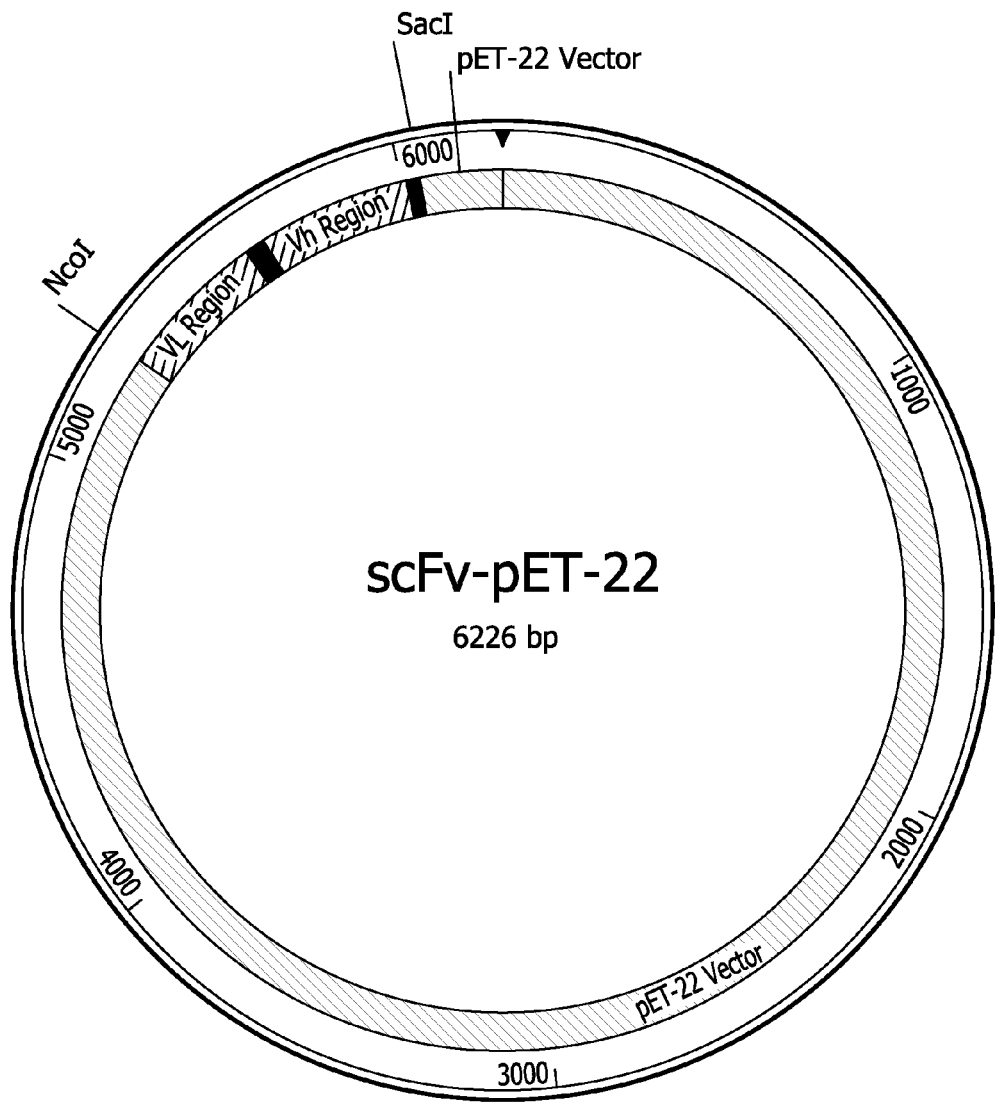
FIG. 4 is a schematic of the scFv construct of FIG. 3 cloned into the pET-22 vector.

The scFv DNA construct was initially cloned into the NcoI/SacI site of the pET-28 (not shown), a vector that does not include any signaling sequences for the secretion of exogenous proteins into the periplasm (EMD Biosciences). Because the expression of exogenous proteins in bacteria is frequently associated with the formation of insoluble aggregates packed into the inclusion bodies, the pET-22 vector was also employed (FIG. 4) (EMD Biosciences). In contrast to the pET-28 vector, the pET-22 vector carries an N-terminal pelB signal sequence for potential periplasmic localization of the expressed protein, a situation in which the produced proteins are potentially more soluble. The two above vectors were tested for their ability to facilitate the production of the scFv variant.

Bacteria expressing the scFv cloned into the pET-22 and pET-28 vectors were cultured in the presence of ampicillin or kanamycin, respectively. After reaching the optical density ($OD_{600}$) of 0.5 units, bacterial cultures were treated with 1 mM isopropyl β-D-1-thiogalactopyranoside (IPTG) to induce the expression of the scFv. Subsequently, the bacterial cultures were incubated for an additional 3 h at 37° C.

Bacteria were collected by centrifugation and then lysed with the B-PER II Protein Extraction Reagent (Thermo Scientific) in the presence of lysozyme, and then the scFv-rich insoluble inclusion bodies were collected by centrifugation. Subsequently, the inclusion bodies were solubilized in 6M guanidinium hydrochloride (GdnHCl) in the presence of the reducing agent dithiothreitol (DTT). Refolding conditions were tested by running pilot-scale refolding assays with the use of the Protein Refolding Kit (Thermo Scientific). As a result of these assays, the denatured scFv molecules present in the GdnHCl-solubilized material were refolded by diluting them into 100 volumes of a refolding buffer consisting of 55 mM Tris, 21 mM NaCl, 0.88 mM KCL, pH 8.2. Subsequently, the sample was concentrated 100-fold by ultrafiltration.

B. scFv Purification and Analyses

Pilot purification of the scFv was carried out with the agarose-conjugated anti-FLAG antibody according to the manufacturer's protocol (Sigma-Aldrich). The purity of purified soluble scFv was analyzed by polyacrylamide gel electrophoresis and by Western blot assay with the anti-FLAG antibody (Sigma-Aldrich) run in denaturing and reducing conditions. The result is shown in FIG. 5A. The electrophoretic migration of the purified scFv indicated the predicted mass.

In addition, due to the relatively high cost of the anti-FLAG antibody, an ion exchange chromatography on the MonoQ Sepharose resin (GE Healthcare Life Sciences) was employed to purify the semi-preparative amounts of the scFv variant. In brief, a sample containing the refolded scFv was loaded onto a MonoQ Sepharose column, and then bound proteins were eluted with a 0-1 M NaCl gradient. The collected peaks were then checked for the presence of the scFv variant by gel electrophoresis assays and Western blot assays with the use of the anti-FLAG antibody (Sigma-Aldrich) (FIG. 5B) in denaturing and reducing conditions. The fraction including the scFv was eluted with 200 mM NaCl, while contaminating proteins were eluted with 500 mM NaCl (FIG. 5B).

Figure 6:
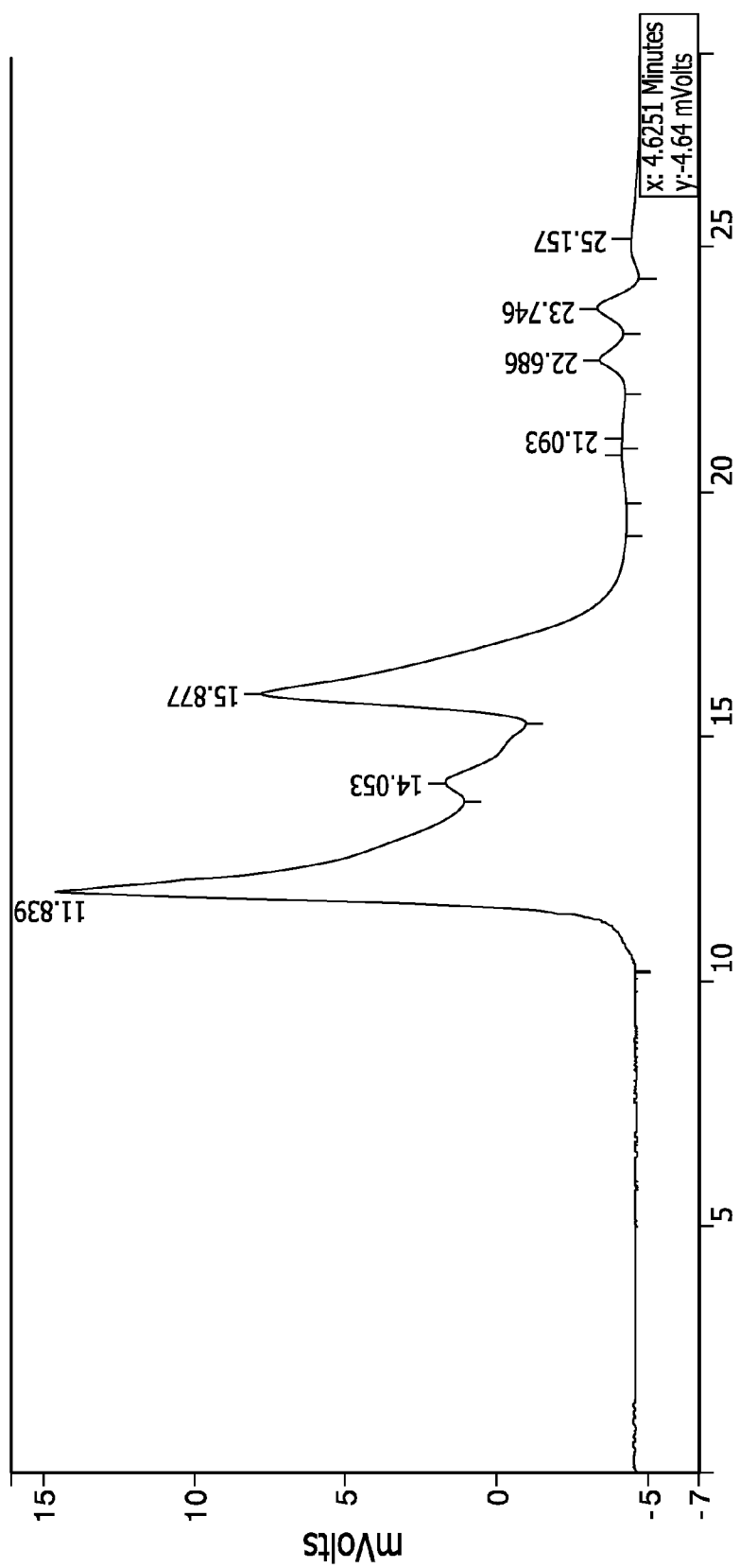
FIG. 6 shows a chromatography profile of the same scFv analyzed by HPLC size exclusion. The three main peaks indicate the single chain antibody monomers and oligomers.

The molecular mass of the purified native scFv was analyzed by high pressure liquid size exclusion chromatography (SEC HPLC) run in non-denaturing conditions. The chromatography profile is shown in FIG. 6. The three main peaks in FIG. 6 indicate the single chain antibody monomers and oligomers.

Figure 7:
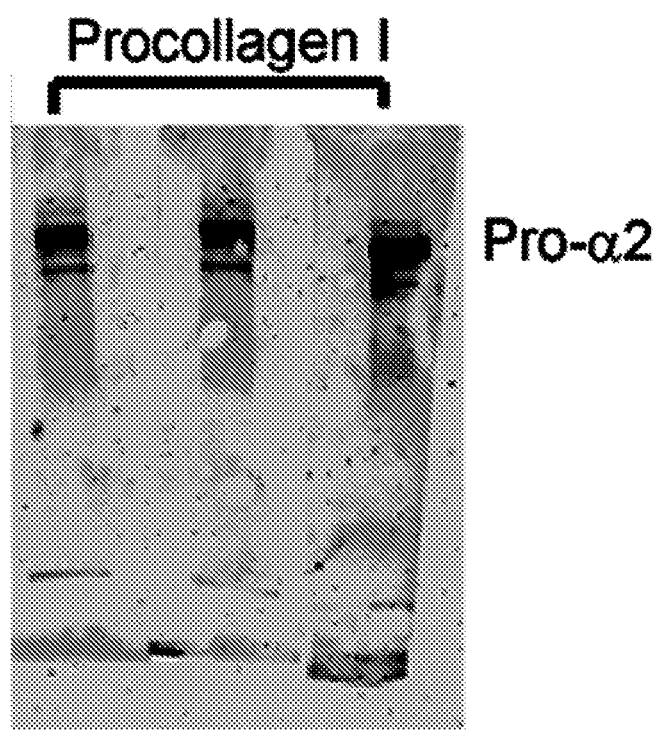
FIG. 7 shows the results of a Western blot analysis of the binding of the same scFv to collagen α2-chain. The lines in FIG. 7 depict different repeats of the assay, and were identified as procollagen I α2 chains, thereby indicating the binding specificity of the single chain antibody for collagen α2-chain.

The binding specificity of the scFv for its intended epitope, the α2-chain of collagen, was confirmed by a Western blot-based assay as follows. Purified human procollagen I was electrophoresed in a polyacrylamide gel. Subsequently, procollagen chains were transferred to a nitrocellulose membrane. Next, the membranes were incubated with FLAG-tagged single chain antibody. The bound single chain antibody was detected with chemiluminescence by an anti-FLAG antibody conjugated to horseradish peroxidase. The results are shown in FIG. 7. The lines in FIG. 7 depict different repeats of the assay, and were identified as procollagen I α2 chains, thereby indicating specific binding of the scFv to collagen α2-chain.

Example 2: Single Chain Antibody Inhibition of Collagen Fibril Deposition

Assays of the inhibition of collagen fibril deposition by the scFv of Example 1 were done in cultures of keloid-derived fibroblasts. In brief, the fibroblasts were seeded into the wells of a 96-well plate at the density of $4 \times 10^3$ cells/well. Six hours after seeding, the attached cell layers were washed and fresh media supplemented with 40 μg/ml of L-ascorbic acid phosphate magnesium salt n-hydrate (Wako Pure Chemical Co.) was added to the cells. Three experimental groups of cells were analysed: (I) non treated, (II) treated with tissue growth factor β (TGF-β) and the scFv, and (III) treated only with TGF-β. TGF-β was added at a concentration of 1 ng/ml, while scFV was added at 1, 5 or 10 μg/ml. The purpose of adding TGF-β, an activator of collagen biosynthesis, was to stimulate cells to produce and secrete high amounts of collagen. After the 48-h culture in the presence or the absence of TGF-β and scFv, layers consisting of collagen-rich extracellular matrix and cells were solubilized by adding a lysis buffer and analyzed by Western blot assays for the presence of collagen I, a main constituent of collagen fibrils. The results shown in FIG. 8 indicate a marked decrease of collagen deposits in a group treated with the scFv. An equal number of cells in the analyzed groups is indicated by comparable amounts of GAPDH. The analyzed groups and the collagen I marker (Cm) are indicated.

Example 3: Constructs for Single-Chain Antibody Production by Yeast Expression

Constructs for the expression of the scFv of Example 1 in yeasts were also engineered. The rationale for employing yeasts to produce the scFv variants was dictated by the fact that those organisms are eukaryotes, a characteristic that potentially may improve the folding and solubility of the recombinant scFv variants.

Accordingly, the following scFv variants were designed: (i) A_L_K, a construct in which a cassette for the $V_H$ of the mouse heavy α chain was linked with a cassette for the $V_L$ of the mouse light κ chain; and (ii) K_L_A, a construct in which a cassette for the $V_L$ of the light κ chain was linked with a cassette for the $V_H$ of the heavy α chain. In comparison to the 15-amino acid linker designed for the bacterial scFv construct (FIG. 3), the scFv constructs for yeast expression consisted of a 30-amino acid linker. See FIGS. 9A-9C. By increasing the length of the linker, the predicted solubility of the A_L_K and K_L_A scFv variants will be higher than that with a shorter linker. Moreover, the increased length of the linker may decrease the potential of scFv variants to form oligomers. If necessary, that the length of the linker may be readily changed by DNA engineering technology.

Figure 9A:
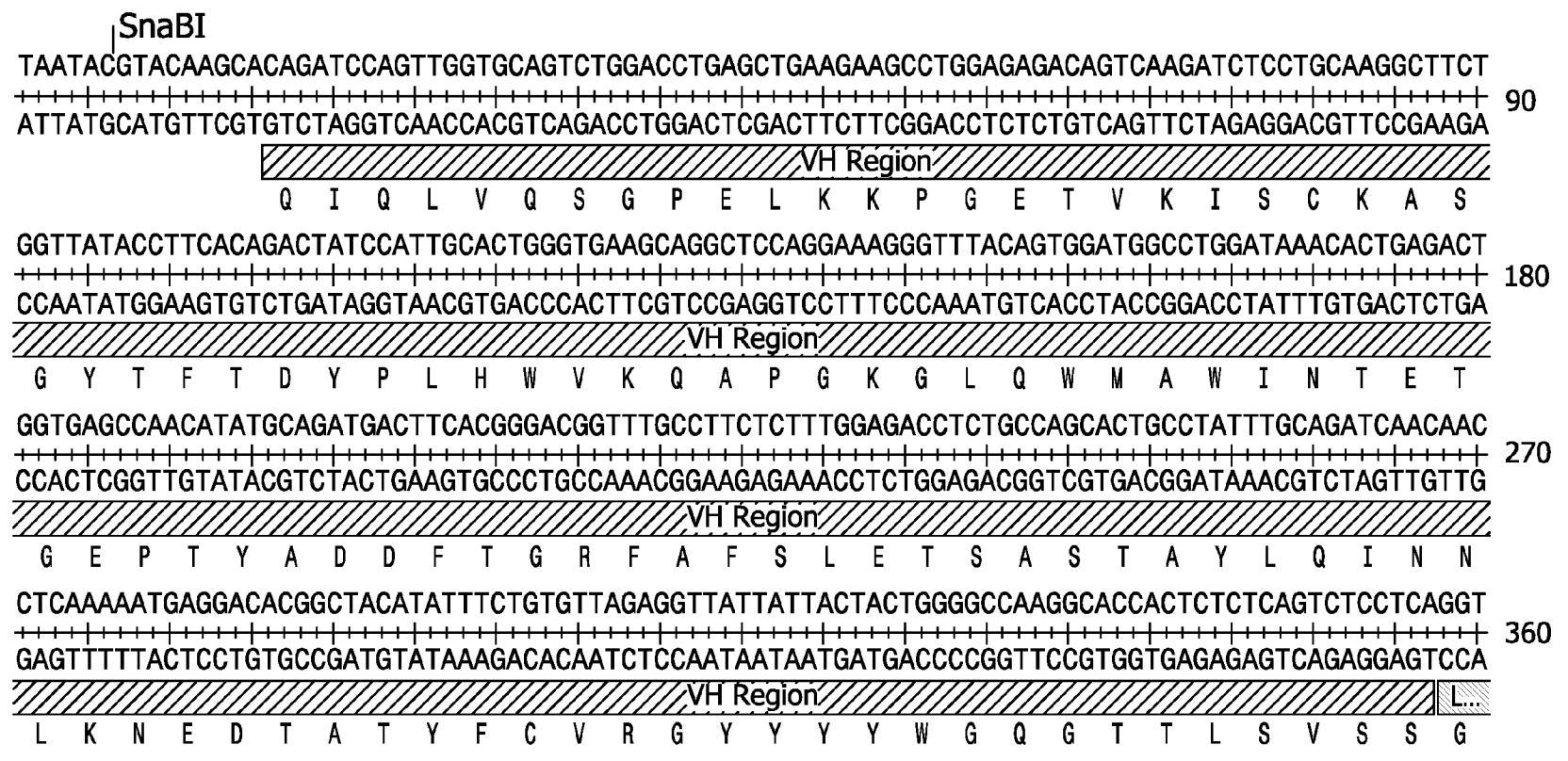
Figure 9B:
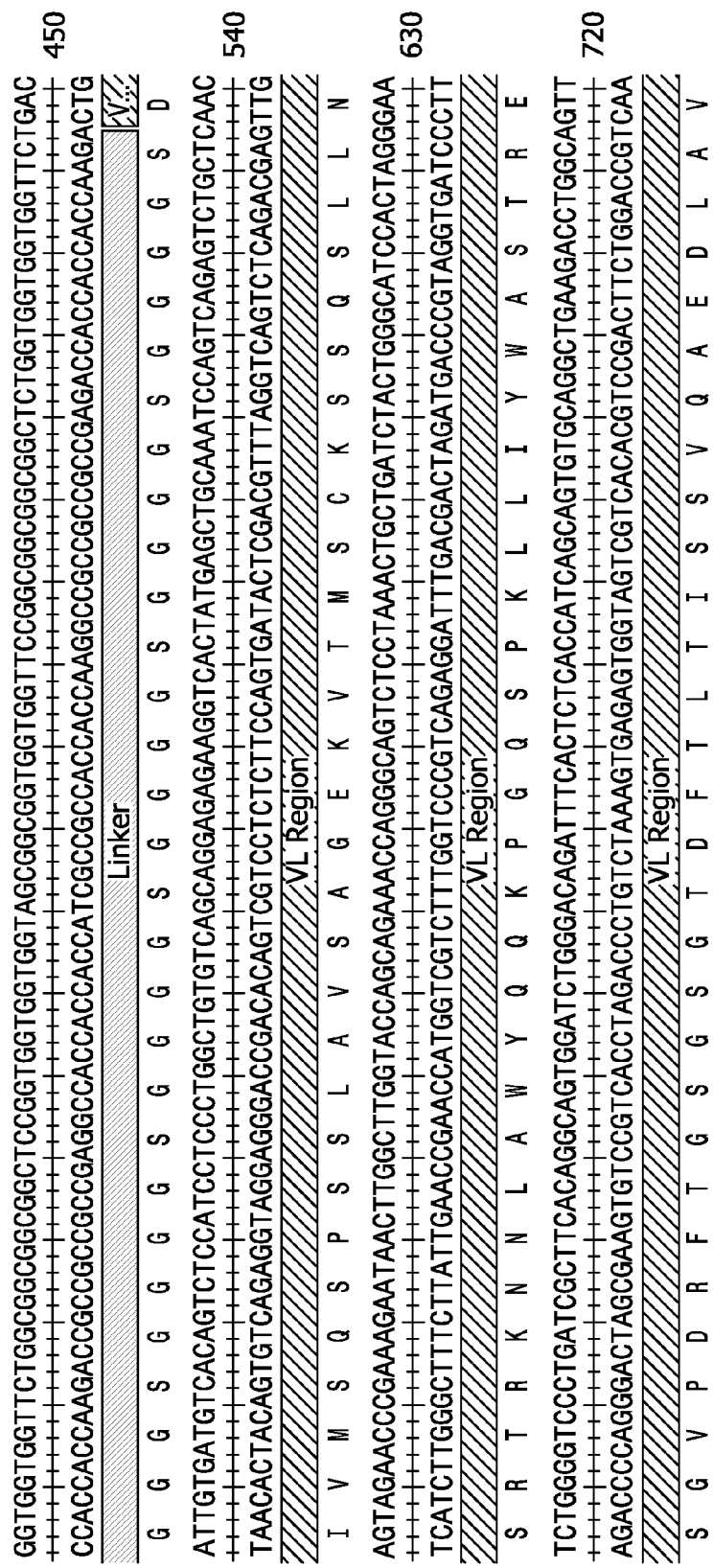
Figure 9C:
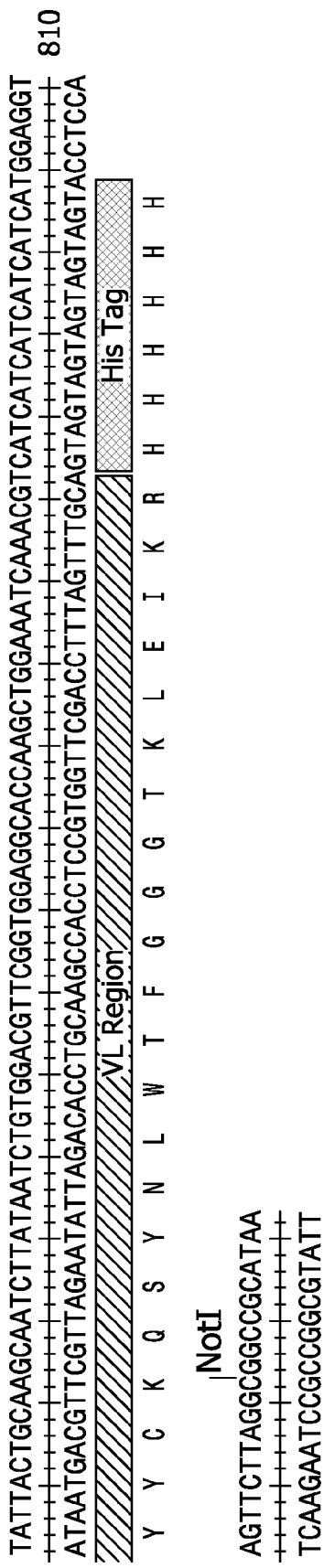
Figure 10:
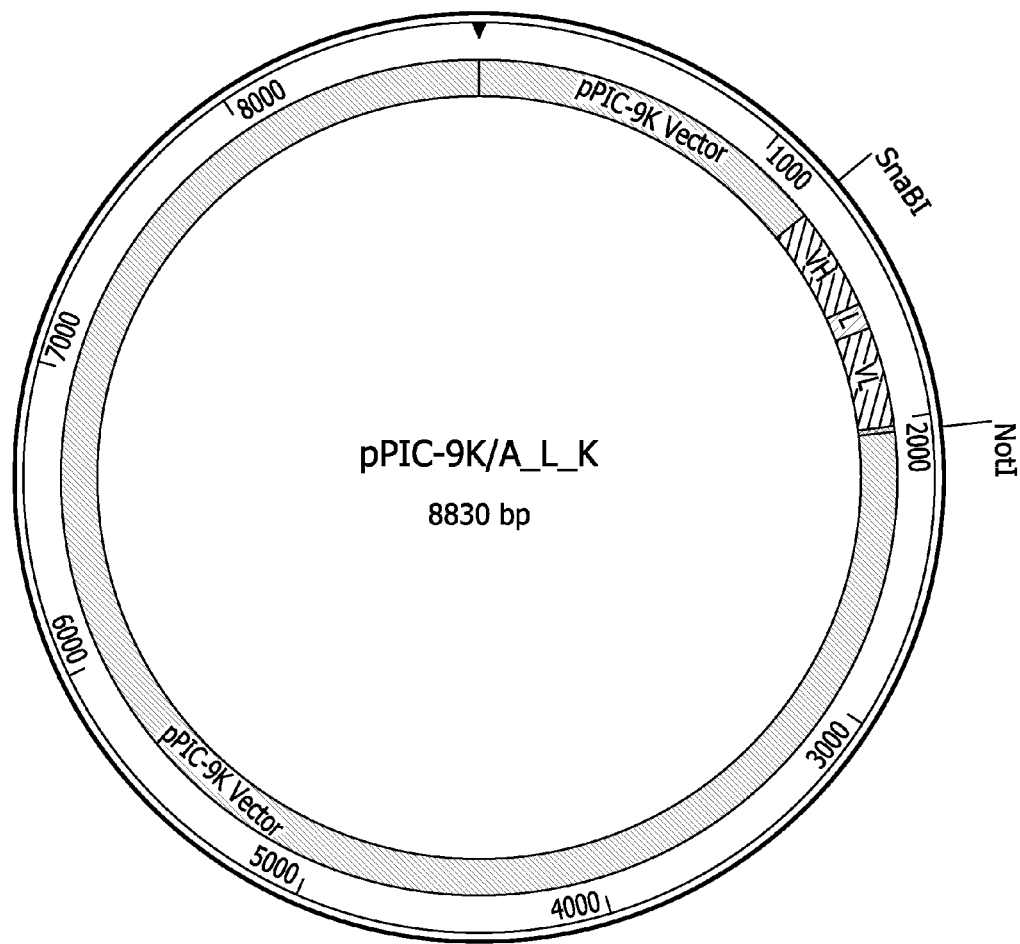
FIG. 10 is a schematic of the scFv construct of FIGS. 9A-9C cloned into the pPIC-9K plasmid. Restriction sites utilized in the cloning strategy are indicated.

The nucleotide (SEQ ID NOS:19 and 30) and amino acid (SEQ ID NO:18) sequences of the A_L_K construct are shown in FIGS. 9A-9C. A schematic of the same construct cloned into the pPIC-9K plasmid is shown in FIG. 10. In both figures, restrictions sites utilized in the cloning strategy are indicated—SnaBI and NotI restriction sites were incorporated at the 5' and 3' ends of the construct, respectively, to facilitate its downstream cloning into the pPIC-9K yeast-expression vector (Invitrogen). A construct for the K_L_A scFv was prepared in a similar way (not shown). The entire DNA constructs for the A_L_K and K_L_A variants were synthesized commercially (Blue Heron Biotechnology, Bothell, Wash. 98021 USA). In both constructs, a His-tag-coding sequence was incorporated to facilitate the downstream purification process (FIGS. 9A-9C). The fidelity of constructs was confirmed by sequencing. The nucleotide and amino acid sequences of the $V_H$-linker-$V_L$ portion of the A_L_K construct (without added restriction sites and His-Tag), comprise SEQ ID NO:17 (nucleotide) and SEQ ID NO:16 (amino acid).

Example 4: Preparation of Chimeric Antibody by Mammalian Cell Expression

Constructs for the mammalian-cell expression of full-length mouse/human chimeric IgG were created. The constructs consist of sequences encoding a mouse variable region fused to sequences encoding constant regions of human to γ and κ chains. Two such DNA constructs were prepared as follows for the expression of a chimeric mouse/human antibody. A first construct encoded a chimera of the mouse-derived heavy chain variable region and a human-derived heavy γ chain ($mV_H$-hγ), while the second construct encoded a chimera of the mouse-derived light chain variable region and a human-derived light κ chain ($mV_L$-hκ).

A. Preparation of DNA Construct for Chimeric Mouse $V_H$-Human Heavy γ Chain ($mV_H$-hγ)

The DNA sequence encoding the $V_H$ region of the heavy mouse α chain of the original anti-α2Ct IgA was cloned into the pETBlue-1 Blunt vector (EMD Biosciences/Novagen). To facilitate downstream cloning into the pFUSE-CHIg-hG1 vector that includes the sequence encoding the constant region (CH) of the heavy γ chain of the human IgG1 (InvivoGen), the EcoRI and NheI restriction sites were introduced via PCR to the DNA sequence encoding the $V_H$ region. See FIG. 11. (The nucleotide and amino acid sequences shown in FIG. 11 are SEQ ID NO:20 and SEQ ID NO:8, respectively.) Subsequently, an insert encoding the $V_H$ region of the heavy mouse α chain was cloned into corresponding restriction sites of the pFUSE-CHIg-hG1 vector (FIG. 12). The fidelity of the $mV_H$-hγ construct was confirmed by DNA sequencing.

B. Preparation of DNA Construct for Chimeric Mouse $V_L$-Human Light κ Chain ($mV_L$-hκ)

DNA sequence encoding the $V_L$ region of the light mouse κ chain of the original anti-α2Ct IgA was cloned into the pETBlue-1 Blunt vector (EMD Biosciences/Novagen). To facilitate downstream cloning into the pFUSE2-CLIg-hκ vector that includes the sequence encoding the constant region (CH) of the human light κ chain (InvivoGen), the AgeI and BsiWI restriction sites were introduced via PCR to the DNA sequence encoding the $V_L$ region of the light mouse κ chain. See FIG. 13. (The nucleotide and amino acid sequences shown in FIG. 13 are SEQ ID NO:21 and SEQ ID NU:7, respectively.) Subsequently, the insert encoding the $V_L$ region of the light mouse κ chain was cloned into the corresponding restriction sites of the pFUSE2-CLIg-hk vector (FIG. 14). The fidelity of the $mV_L$-hκ construct was confirmed by DNA sequencing.

C. Selection of Clones Expressing Chimeric $mV_H$-hγ and $mV_L$-hκ Variants in Mammalian Cells Chimeric variants were expressed in Chinese hamster ovary cells (CHO). In brief, CHO cells were transfected with a DNA construct encoding the $mV_H$-hγ variant. Zeocin-resistant clones were selected and screened for the presence of the $mV_H$-hγ. Specifically, proteins secreted to the media by selected clones were analyzed by Western blot for the presence of the $mV_H$-hγ variant with the use of the goat anti-human γ chain polyclonal antibody conjugated with HRP (Sigma-Aldrich). Next, the selected γ chain-positive CHO clone was expanded in cell culture and then transfected with a DNA construct encoding the $mV_L$-hκ variant. Subsequently, cell culture media from the double-transfected clones resistant to Zeocin and Blasticidin were analyzed by Western blot for the production of the $mV_L$-hκ chain with the use of the polyclonal goat anti-human k chain antibodies conjugated with HRP. Selected clones stably co-expressing $mV_H$-hγ and $mV_L$-hκ chains were expanded in cell culture and then cryopreserved in liquid nitrogen.

D. Purification of the Chimeric Antibody Consisting of the $mV_H$-hγ and $mV_L$-hκ Chains Cell culture media from selected CHO cells producing the chimeric antibody were collected. Subsequently, proteins secreted to the media were precipitated with ammonium sulfate added to a 50-% saturation. Precipitated proteins were collected by centrifugation and then the protein pellet was solubilized in phosphate buffered saline (PBS). Insoluble material was removed by centrifugation while the supernatant was collected for further processing. The chimeric IgG was purified by employing the Protein-L agarose (Thermo Scientific), a resin that specifically binds to the κ chain of human but not bovine origin.

Figure 15A:
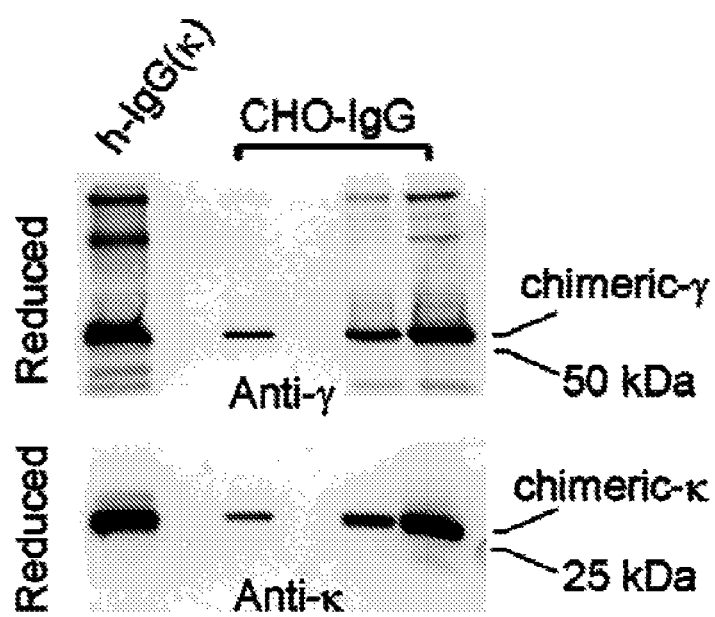
FIG. 15A is a Western blot analysis under reducing conditions showing that specific antibodies against IgG γ and κ chains (Anti-γ; Anti-κ) reacted with a chimeric antibody of the invention secreted by CHO cells. The results confirm the presence of γ and κ chains in the chimeric antibody (chimeric-γ; chimeric-κ). Human IgG containing a κ chain was used as positive marker (h-IgG(κ)). The chimeric antibody was composed of a murine heavy α chain variable region (SEQ ID NO:8)/human γ constant region chain and a murine light chain κ region (SEQ ID NO:7)/human κ constant region chain.
Figure 15B:
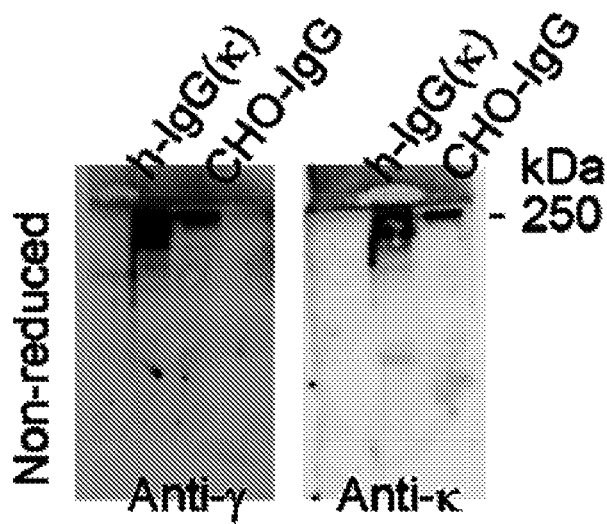
FIG. 15B is a Western blot analysis of the same chimeric antibody under non-reducing conditions with anti-human γ and anti-human κ antibodies. The results indicate that the antibody heavy and light chains (the component $mV_H$-hγ and $mV_L$-hκ chains) were covalently linked via disulfide bonds, thereby indicating the formation of the chimeric antibody. The presence of a high molecular band (CHO-IgG) indicates production of chimeric IgG molecules by the CHO cells. Human IgG with the κ chain was used as positive marker (h-IgG(κ)).

Purified chimeric antibodies were analyzed in reducing conditions for the presence of the γ and κ chains. Specific antibodies against particular chains confirm the production of the γ and κ chains by CHO cells (FIG. 15A). To determine if the two chains of the chimeric IgG antibody, i.e., $mV_H$-hγ and $mV_L$-hκ chains, co-assemble into native-like molecules consisting of both types of chains linked via disulfide bonds, the purified proteins secreted from CHO cells were separated in a polyacrylamide gel in non-reducing conditions. Subsequent Western blot assays with the anti-human γ chain and the anti human κ chain antibodies indicate that $mV_H$-hγ and $mV_L$-hκ chains were covalently linked via disulfide bonds, thereby indicating the formation of chimeric antibody molecules consisting of heavy and light chains of expected molecular mass (FIG. 15B.). The presence of a high molecular band indicates production of chimeric IgG molecules by CHO cells. Human IgG with the chain was used as a positive marker (h-IgG(κ)).

E. Binding of the Chimeric IgG to its Designated Target

Figure 16:
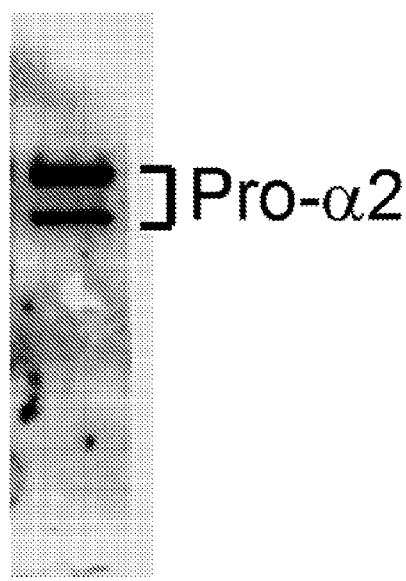
FIG. 16 is a Western blot assay showing the binding of the purified chimeric antibody to its target, α2Ct, as detected by chemiluminescence with the use of the anti-human γ antibodies conjugated with horseradish peroxidase (HRP). Positive bands were identified as those corresponding to intact procollagen I α2 chain (upper band) and its partially degraded form. Native human IgG with the κ chain was used as a positive marker (Bethyl Laboratories Inc.).

Western blot assays were employed to test the binding of purified chimeric IgG to its designated target, i.e., the C terminal telopeptide of the α2 chain of human procollagen I (α2Ct). In brief, the al and α2 chains of procollagen I purified from the cultured of human dermal fibroblasts were separated in a polyacrylamide gel followed by their transfer into a nitrocellulose membrane. Subsequently, the membrane was incubated with chimeric IgG solubilized in a blocking buffer. The binding of the chimeric IgG to the α2Ct was detected by chemiluminescence with the use of the anti-human γ antibodies conjugated with horseradish peroxidase (HRP), as shown in FIG. 16. Positive bands were identified as those corresponding to intact procollagen I α2 chain (upper band) and its partially degraded form. Native human IgG with the κ chain was used as a positive marker (Bethyl Laboratories Inc.).

Example 5: Binding Kinetics of Anti-α2Ct Variants to Human Procollagen

Figure 17:
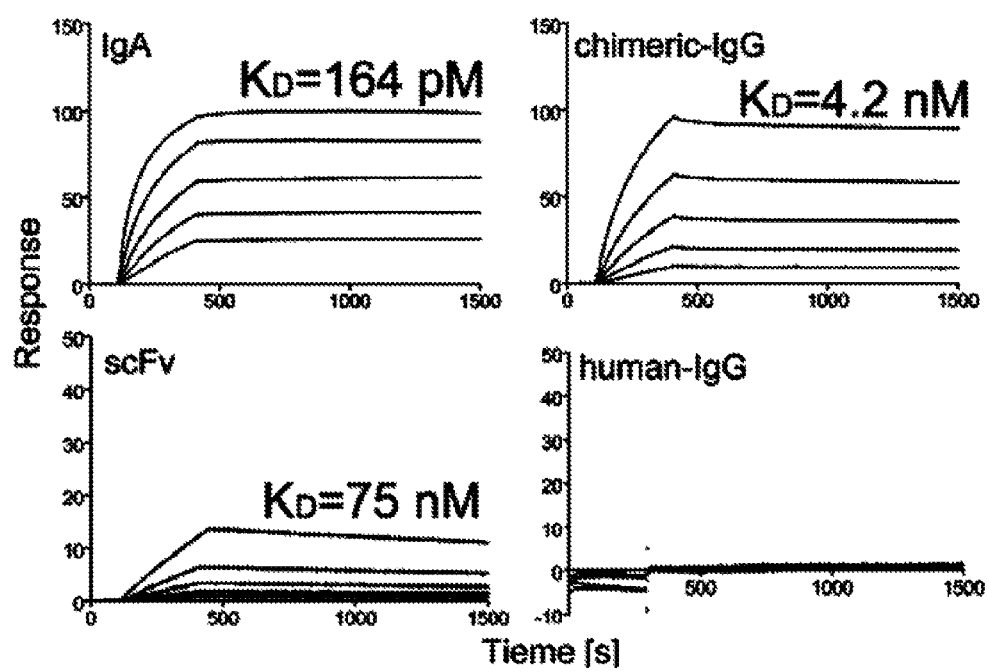
FIG. 17 shows association and dissociation curves illustrating kinetics of the binding between procollagen and the following anti-α2Ct antibody variants: the original anti-α2Ct mouse IgA antibody (IgA) from which the $mV_H$ and $mV_L$ were obtained; the bacterial-derived scFv variant (scFv) of FIG. 3; the mouse-human chimeric IgG (chimeric IgG); and human IgG with the light κ chain (human-IgG) (control). In each panel, the curves represent association and dissociation events during the interaction between immobilized procollagen I and free antibody variants present at concentrations ranging from $4 \times 10^{-7}$ M to $1.25 \times 10^{-8}$ M. For each assay, the association rate constants ($k_{on}$) and the dissociation rate constants ($k_{off}$) were obtained, and the equilibrium dissociation constants ($K_D$) values were calculated from a ratio of $k_{off}/k_{on}$.

The binding of the anti-α2Ct variants (scFv and chimeric-Ig) to human procollagen I was analyzed with the use of the SensiQ Pioneer biosensor (ICx Nomadics). In brief, purified human procollagen I, a protein that includes a native α2 C telopeptide, was covalently immobilized on a sensor chip (COOH2, ICx Nomadics). Subsequently, the kinetics of the binding of the original anti-α2Ct mouse IgA antibody, the binding of the bacterial-derived scFv variant of Example 1, and the binding of the mouse-human chimeric IgG of Example 4, were analyzed. Human IgG with the light κ chain was used as a control (Bethyl Laboratories, Inc.). The dissociation equilibrium constant ($K_D$) values for each interaction were calculated with the use of the QDat software (ICx Nomadics). The results are show in FIG. 17. In each panel, the curves represent association and dissociation events during the interaction between immobilized procollagen I and free antibody variants present at concentrations ranging from $4\times10^{-7}$ M to $1.25\times10^{-8}$ M. For each assay, the association rate constants ($k_{on}$) and the dissociation rate constants ($k_{off}$) were obtained, and the equilibrium dissociation constants ($K_D$) values were calculated from a ratio of $k_{off}/k_{on}$. Although specific $K_D$ values differ, all variants are characterized by a strong binding affinity to procollagen I. The lack of binding of control human IgG to procollagen I indicates the high specificity of the presented binding assays.

Example 6: Expression, Purification and Testing of scFv Variants Produced in Yeast A. Expression of scFv in Yeasts Yeast clones expressing the A_L_K or K_L_A scFv variants cloned into the pPIC-9K yeast-expression vector according to Example 3 were selected by culturing them in the absence of histidine (His(−) conditions) according to manufacturer's suggestions (Invitrogen). Subsequently, the selected clones were tested for production of the scFv variants. In brief, the selected clones were cultured in the presence of methanol as a sole source of carbon. After six days cell culture media were tested for the presence of secreted scFv variants. Specifically, His-tagged scFv variants were detected by Western blot assays in which the anti-His tag antibody was employed. In addition to Western blot assays, PCR was employed to confirm the presence of DNA encoding the specific scFv variants in the yeasts' genome.

Figure 18A:
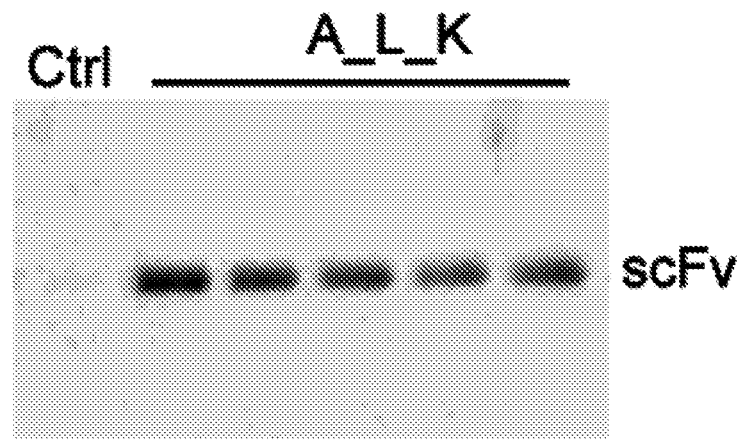
FIG. 18A is a Western blot assay of scFv variant prepared in yeast from the A_L_K construct. The lanes show the secretion of various yeast clones cultured in His(−) conditions. Cell culture media from non-transformed yeast cells (left lane, "Ctrl") are negative for the scFv variant.
Figure 18B:
FIG. 18B shows the result of PCR assays of yeast clones producing scFv variants from the A_L_K DNA construct, and from another DNA construct, K_L_A. The presence of the DNA constructs in the genomes of the analyzed clones is indicated.

The results are shown in FIGS. 18A (Western blot assay) and 18B (PCR assay). Because of noticeably smaller yield of the K_L_A variant (not shown), only the A_L_K scFv construct was chosen for further analyses. As shown in FIG. 18A, Western blot assays of the A_L_K scFv variant secreted by various yeast clones cultured in His(−) conditions stained positive for His-tagged scFv variant. Cell culture media from non-transformed yeast cells (Ctrl) are negative for the scFv variant. As shown in FIG. 148, PCR assay confirmed the presence of DNA constructs encoding the A_L_K and K_L_A variants in the genome of analyzed clones.

B. Purification of Yeast scFv Variants

Purification of the scFv variants was carried out with a nickel column according to the manufacturer's protocol (Invitrogen). The His-tagged A_L_K was purified on the nickel column. The purified scFv variants were analyzed by gel electrophoresis and by Western blot assays run in denaturing and reducing conditions. Furthermore, the molecular mass of the purified native scFv was analyzed by high pressure liquid size exclusion chromatography (SEC HPLC) run in non-denaturing conditions.

Figure 19:
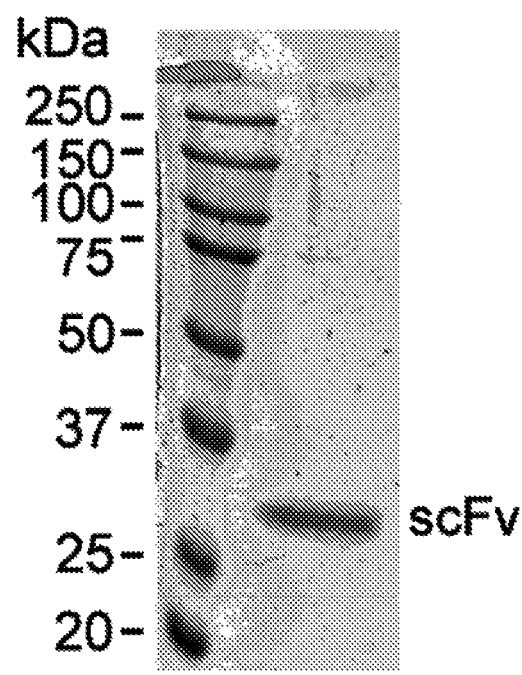
FIG. 19 shows an electrophoretic assay of the A_L_K yeast scFv variant after purification by nickel column. Electrophoretic migration of the purified scFv in denaturing/reducing conditions indicates its predicted mass.

As indicated in FIG. 19, the A_L_K scFv variant eluted from the nickel column contributed the main band seen in the electrophoretic gel. In the denaturing/reducing conditions of the assay, the A_L_K scFv variant purified from yeast cultures migrated in the electrophoretic field according to its predicted mass of 28 kDa. SEC HPLC assays (not shown), however, demonstrate that in the applied native conditions, most of the concentrated scFv molecules (concentration of 0.6 mg/ml) aggregate to form high-molecular mass assemblies. Such aggregate formation is a common characteristic of recombinant proteins, and may be remedied by optimization of experimental conditions in which aggregate formation is minimized.

C. Western Blot Assays of scFv Binding to its Designated Target

Figure 20:
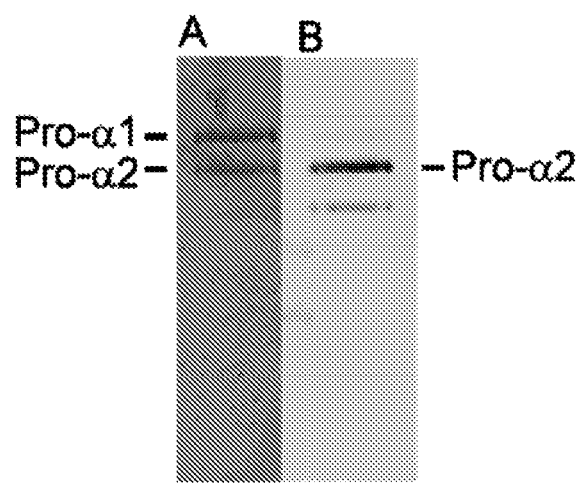
FIG. 20 is a Western blot analysis showing in lane (A) electrophoresis of the purified human procollagen I in a polyacrylamide gel, showing staining of procollagen I α1 and α2 chains. The procollagen chains were transferred to a nitrocellulose membrane and probed with His-tagged yeast-derived A_L_K scFv variant. The A_L_K scFv variant bound to its specific target procollagen I α2 chain, as shown in lane (B).

Western blot assays were employed to test the binding of purified scFv to its designated target i.e. the C terminal telopeptide of the α2 chain of human procollagen I (α2Ct). In brief, the Pro-al and Pro-α2 chains of procollagen I purified from the culture of human dermal fibroblasts were separated in a polyacrylamide gel followed by their transfer into a nitrocellulose membrane. Subsequently, the nitrocellulose membrane was incubated with scFv. The binding of the His-tagged scFv to the α2Ct was detected by chemiluminescence with the use of the anti-His antibodies conjugated with horseradish peroxidase (HRP). The results, shown in FIG. 20. Lane (A) represents the electrophoresis of the purified human procollagen I in a polyacrylamide gel (Coomassie blue-stained chains are indicated). Lane B represents the nitrocellulose membrane incubated with His-tagged yeast-derived scFv. The presented protein band (Lane B) was identified as procollagen I α2 chain, thereby indicating specific scFv-α2Ct binding.

The disclosures of each and every patent, patent application, publication and GenBank record cited herein are hereby incorporated herein by reference in their entirety.

One skilled in the art will readily appreciate that the present invention is well adapted to carry out the objects and obtain the ends and advantages mentioned, as well as those inherent therein. While the invention has been disclosed with reference to specific embodiments, it is apparent that other embodiments and variations of this invention may be devised by others skilled in the art without departing from the true spirit and scope used in the practice of the invention. The appended claims are intended to be construed to include all such embodiments and equivalent variations.

What is claimed is:

1. A chimeric, humanized, or single-chain antibody which comprises a light chain variable region comprising complementarity determining regions comprising the amino acid sequences SEQ ID NO:1, SEQ ID NO:2, and SEQ ID NO:3, and a heavy chain variable region comprising complementarity determining regions comprising the amino acid sequences SEQ ID NO:4, SEQ ID NO:5, and SEQ ID NO:6, or a fragment of said chimeric or humanized antibody, which antibody or antibody fragment binds the C-terminal telopeptide of the α2(I) chain of human collagen I.

2. The antibody or antibody fragment according to claim 1, which is a chimeric antibody or fragment of a chimeric antibody, which fragment binds the C-terminal telopeptide of the α2(I) chain of human collagen.

3. The chimeric antibody according to claim 2, which comprises an antibody light chain comprising a light variable region having the amino acid sequence shown in SEQ ID NO:10, and an antibody heavy chain comprising a heavy chain variable region having the amino acid sequence SEQ ID NO:11, or a fragment of said chimeric antibody which binds the C-terminal telopeptide of the α2(I) chain of human collagen.

4. The chimeric antibody according to claim 3, wherein said antibody light chain comprises a human antibody light chain constant region, and said antibody heavy chain comprises a human antibody heavy chain constant region, or a fragment of said chimeric antibody which binds the C-terminal telopeptide of the α2(I) chain of human collagen.

5. The chimeric antibody according to claim 4, wherein the human constant regions comprise IgG constant regions.

6. The antibody or antibody fragment according to claim 1, which is a humanized antibody or fragment of a humanized antibody, which fragment binds the C-terminal telopeptide of the α2(I) chain of human collagen.

7. The humanized antibody according to claim 6, which comprises a human antibody framework region and/or a human antibody constant region, or a fragment of said humanized antibody which binds the C-terminal telopeptide of the α2(I) chain of human collagen.

8. The humanized antibody according to claim 6, which comprises a human antibody constant region.

9. The humanized antibody according to claim 8, wherein the constant region comprises an IgG constant region.

10. The antibody according to claim 1, which is a single chain antibody.

11. The single chain antibody according to claim 10, wherein the single chain antibody comprises a light chain variable region having the amino acid sequence shown in SEQ ID NO:10, and a heavy chain variable region having the amino acid sequence shown in SEQ ID NO:11.

12. The single chain antibody according to claim 11, wherein the antibody further comprises a linker comprising a sequence of one or more amino acids linking said light chain variable region and said heavy chain variable region.

13. The single chain antibody according to claim 12, wherein the linker comprises the amino acid sequence Gly-Gly-Ser or the amino acid sequence Gly-Gly-Gly-Gly-Ser (SEQ ID NO:29).

14. The single chain antibody according to claim 12, wherein the linker connects the carboxy terminus of said light chain variable region to the amino terminus of said heavy chain variable region.

15. The single chain antibody according to claim 13, wherein the linker comprises from two to twelve repeats of the amino acid sequence Gly-Gly-Ser, or from two to twelve repeats of the amino acid sequence Gly-Gly-Gly-Gly-Ser (SEQ ID NO:29).

16. The single chain antibody according to claim 15, comprising the amino acid sequence shown in SEQ ID NO:12.

17. The single chain antibody according to claim 12, wherein the linker connects the carboxy terminus of said heavy chain variable region to the amino terminus of said light chain variable region.

18. The single chain antibody according to claim 17, wherein the linker comprises from two to twelve repeats of the amino acid sequence Gly-Gly-Ser, or from two to twelve repeats of the amino acid sequence Gly-Gly-Gly-Gly-Ser (SEQ ID NO:29).

19. The single chain antibody according to claim 18, comprising the amino acid sequence shown in SEQ ID NO:16.

20. A pharmaceutical composition comprising the antibody or antibody fragment according to claim 1 and a pharmaceutically acceptable carrier.

* * * * *

SEQUENCE LISTING

<160> NUMBER OF SEQ ID NOS: 30

<210> SEQ ID NO 1
<211> LENGTH: 17
<212> TYPE: PRT
<213> ORGANISM: Mus musculus

<400> SEQUENCE: 1

Lys Ser Ser Gln Ser Leu Leu Asn Ser Arg Thr Arg Lys Asn Asn Leu
1               5                   10                  15

Ala

<210> SEQ ID NO 2
<211> LENGTH: 7
<212> TYPE: PRT
<213> ORGANISM: Mus musculus

<400> SEQUENCE: 2

Trp Ala Ser Thr Arg Glu Ser
1               5

<210> SEQ ID NO 3
<211> LENGTH: 8
<212> TYPE: PRT
<213> ORGANISM: Mus musculus

<400> SEQUENCE: 3

Lys Gln Ser Tyr Asn Leu Trp Thr
1               5

<210> SEQ ID NO 4
<211> LENGTH: 16
<212> TYPE: PRT
<213> ORGANISM: Mus musculus

<400> SEQUENCE: 4

Gln Ile Gln Leu Val Gln Ser Gly Pro Glu Leu Lys Lys Pro Gly Glu
1               5                   10                  15

<210> SEQ ID NO 5
<211> LENGTH: 19
<212> TYPE: PRT
<213> ORGANISM: Mus musculus

<400> SEQUENCE: 5

Met Ala Trp Ile Asn Thr Glu Thr Gly Glu Pro Thr Tyr Ala Asp Asp
1               5                   10                  15

Phe Thr Gly

<210> SEQ ID NO 6
<211> LENGTH: 5
<212> TYPE: PRT
<213> ORGANISM: Mus musculus

<400> SEQUENCE: 6

Gly Tyr Tyr Tyr Tyr
1               5

<210> SEQ ID NO 7
<211> LENGTH: 128
<212> TYPE: PRT
<213> ORGANISM: Mus musculus
<220> FEATURE:
<221> NAME/KEY: SIGNAL

<222> LOCATION: (1)..(15)

<400> SEQUENCE: 7

Met Val Leu Met Leu Leu Leu Trp Val Ser Gly Thr Cys Gly Asp
1               5                   10                  15

Ile Val Met Ser Gln Ser Pro Ser Ser Leu Ala Val Ser Ala Gly Glu
            20                  25                  30

Lys Val Thr Met Ser Cys Lys Ser Ser Gln Ser Leu Leu Asn Ser Arg
        35                  40                  45

Thr Arg Lys Asn Asn Leu Ala Trp Tyr Gln Gln Lys Pro Gly Gln Ser
    50                  55                  60

Pro Lys Leu Leu Ile Tyr Trp Ala Ser Thr Arg Glu Ser Gly Val Pro
65                  70                  75                  80

Asp Arg Phe Thr Gly Ser Gly Ser Gly Thr Asp Phe Thr Leu Thr Ile
                85                  90                  95

Ser Ser Val Gln Ala Glu Asp Leu Ala Val Tyr Tyr Cys Lys Gln Ser
            100                 105                 110

Tyr Asn Leu Trp Thr Phe Gly Gly Gly Thr Lys Leu Glu Ile Lys Arg
        115                 120                 125

<210> SEQ ID NO 8
<211> LENGTH: 133
<212> TYPE: PRT
<213> ORGANISM: Mus musculus
<220> FEATURE:
<221> NAME/KEY: SIGNAL
<222> LOCATION: (1)..(19)

<400> SEQUENCE: 8

Met Gly Trp Val Trp Asn Leu Leu Phe Leu Met Ala Ala Ala Gln Cys
1               5                   10                  15

Ile Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
        35                  40                  45

Thr Asp Tyr Pro Leu His Trp Val Lys Gln Ala Pro Gly Lys Gly Leu
    50                  55                  60

Gln Trp Met Ala Trp Ile Asn Thr Glu Thr Gly Glu Pro Thr Tyr Ala
65                  70                  75                  80

Asp Asp Phe Thr Gly Arg Phe Ala Phe Ser Leu Glu Thr Ser Ala Ser
                85                  90                  95

Thr Ala Tyr Leu Gln Ile Asn Asn Leu Lys Asn Glu Asp Thr Ala Thr
            100                 105                 110

Tyr Phe Cys Val Arg Gly Tyr Tyr Tyr Trp Gly Gln Gly Thr Thr
        115                 120                 125

Leu Ser Val Ser Ser
    130

<210> SEQ ID NO 9
<211> LENGTH: 112
<212> TYPE: PRT
<213> ORGANISM: Mus

<400> SEQUENCE: 9

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Asn Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Lys Gln
                 85                  90                  95

Ser Tyr Asn Leu Trp Thr Phe Gly Gly Gly Thr Lys Leu Glu Ile Lys
            100                 105                 110

<210> SEQ ID NO 10
<211> LENGTH: 113
<212> TYPE: PRT
<213> ORGANISM: Mus musculus

<400> SEQUENCE: 10

Asp Ile Val Met Ser Gln Ser Pro Ser Ser Leu Ala Val Ser Ala Gly
 1               5                  10                  15

Glu Lys Val Thr Met Ser Cys Lys Ser Ser Gln Ser Leu Leu Asn Ser
             20                  25                  30

Arg Thr Arg Lys Asn Asn Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Lys Gln
                 85                  90                  95

Ser Tyr Asn Leu Trp Thr Phe Gly Gly Gly Thr Lys Leu Glu Ile Lys
            100                 105                 110

Arg

<210> SEQ ID NO 11
<211> LENGTH: 114
<212> TYPE: PRT
<213> ORGANISM: Mus musculus

<400> SEQUENCE: 11

Gln Ile Gln Leu Val Gln Ser Gly Pro Glu Leu Lys Lys Pro Gly Glu
 1               5                  10                  15

Thr Val Lys Ile Ser Cys Lys Ala Ser Gly Tyr Thr Phe Thr Asp Tyr
             20                  25                  30

Pro Leu His Trp Val Lys Gln Ala Pro Gly Lys Gly Leu Gln Trp Met
            35                  40                  45

Ala Trp Ile Asn Thr Glu Thr Gly Glu Pro Thr Tyr Ala Asp Asp Phe
 50                  55                  60

Thr Gly Arg Phe Ala Phe Ser Leu Glu Thr Ser Ala Ser Thr Ala Tyr
 65                  70                  75                  80

Leu Gln Ile Asn Asn Leu Lys Asn Glu Asp Thr Ala Thr Tyr Phe Cys
                 85                  90                  95

Val Arg Gly Tyr Tyr Tyr Trp Gly Gln Gly Thr Thr Leu Ser Val
            100                 105                 110

Ser Ser

<210> SEQ ID NO 12
<211> LENGTH: 246
<212> TYPE: PRT
<213> ORGANISM: Artificial Sequence
<220> FEATURE:
<223> OTHER INFORMATION: Recombinantly produced single chain antibody

<400> SEQUENCE: 12

```
Met Asp Ile Val Met Ser Gln Ser Pro Ser Ser Leu Ala Val Ser Ala
1               5                   10                  15

Gly Glu Lys Val Thr Met Ser Cys Lys Ser Ser Gln Ser Leu Leu Asn
            20                  25                  30

Ser Arg Thr Arg Lys Asn Asn Leu Ala Trp Tyr Gln Gln Lys Pro Gly
        35                  40                  45

Gln Ser Pro Lys Leu Leu Ile Tyr Trp Ala Ser Thr Arg Glu Ser Gly
    50                  55                  60

Val Pro Asp Arg Phe Thr Gly Ser Gly Ser Gly Thr Asp Phe Thr Leu
65                  70                  75                  80

Thr Ile Ser Ser Val Gln Ala Glu Asp Leu Ala Val Tyr Tyr Cys Lys
                85                  90                  95

Gln Ser Tyr Asn Leu Trp Thr Phe Gly Gly Gly Thr Lys Leu Glu Ile
            100                 105                 110

Lys Val Asp Gly Gly Gly Ser Gly Gly Gly Ser Gly Gly Gly
        115                 120                 125

Gly Ser Leu Glu Gln Ile Gln Leu Val Gln Ser Gly Pro Glu Leu Lys
    130                 135                 140

Lys Pro Gly Glu Thr Val Lys Ile Ser Cys Lys Ala Ser Gly Tyr Thr
145                 150                 155                 160

Phe Thr Asp Tyr Pro Leu His Trp Val Lys Gln Ala Pro Gly Lys Gly
                165                 170                 175

Leu Gln Trp Met Ala Trp Ile Asn Thr Glu Thr Gly Glu Pro Thr Tyr
            180                 185                 190

Ala Asp Asp Phe Thr Gly Arg Phe Ala Phe Ser Leu Glu Thr Ser Ala
        195                 200                 205

Ser Thr Ala Tyr Leu Gln Ile Asn Asn Leu Lys Asn Glu Asp Thr Ala
    210                 215                 220

Thr Tyr Phe Cys Val Arg Gly Tyr Tyr Tyr Trp Gly Gln Gly Thr
225                 230                 235                 240

Thr Leu Ser Val Ser Ser
            245
```

<210> SEQ ID NO 13
<211> LENGTH: 738
<212> TYPE: DNA
<213> ORGANISM: Artificial Sequence
<220> FEATURE:
<223> OTHER INFORMATION: Recombinantly produced polynucleotide encoding single chain antibody of SEQ ID NO:12

<400> SEQUENCE: 13

```
atggacattg tgatgtcaca gtctccatcc tccctggctg tgtcagcagg agagaaggtc      60
actatgagct gcaaatccag tcagagtctg ctcaacagta aacccgaaa gaataacttg     120 gcttggtacc agcagaaacc agggcagtct cctaaactgc tgatctactg ggcatccact     180
agggaatctg ggtccctga tcgcttcaca ggcagtggat ctgggacaga tttcactctc     240
accatcagca gtgtgcaggc tgaagacctg gcagtttatt actgcaagca atcttataat     300
ctgtggacgt tcggtggagg caccaagctg gaaatcaaag tcgacggtgg tggtggttct     360
```

```
ggcggcggcg gctccggtgg tgtggttct ctcgagcaga tccagttggt gcagtctgga    420
cctgagctga agaagcctgg agagacagtc aagatctcct gcaaggcttc tggttatacc    480
ttcacagact atccattgca ctgggtgaag caggctccag gaaagggttt acagtggatg    540
gcctggataa acactgagac tggtgagcca acatatgcag atgacttcac gggacggttt    600
gccttctctt tggagacctc tgccagcact gcctatttgc agatcaacaa cctcaaaaat    660
gaggacacgg ctacatattt ctgtgttaga ggttattatt actactgggg ccaaggcacc    720
actctctcag tctcctca                                                  738
```

```
<210> SEQ ID NO 14
<211> LENGTH: 254
<212> TYPE: PRT
<213> ORGANISM: Artificial Sequence
<220> FEATURE:
<223> OTHER INFORMATION: Recombinantly produced single chain antibody
      comprising C-terminal FLAG tag

<400> SEQUENCE: 14

Met Asp Ile Val Met Ser Gln Ser Pro Ser Ser Leu Ala Val Ser Ala
1               5                   10                  15

Gly Glu Lys Val Thr Met Ser Cys Lys Ser Ser Gln Ser Leu Leu Asn
            20                  25                  30

Ser Arg Thr Arg Lys Asn Asn Leu Ala Trp Tyr Gln Gln Lys Pro Gly
        35                  40                  45

Gln Ser Pro Lys Leu Leu Ile Tyr Trp Ala Ser Thr Arg Glu Ser Gly
    50                  55                  60

Val Pro Asp Arg Phe Thr Gly Ser Gly Ser Gly Thr Asp Phe Thr Leu
65                  70                  75                  80

Thr Ile Ser Ser Val Gln Ala Glu Asp Leu Ala Val Tyr Tyr Cys Lys
                85                  90                  95

Gln Ser Tyr Asn Leu Trp Thr Phe Gly Gly Gly Thr Lys Leu Glu Ile
            100                 105                 110

Lys Val Asp Gly Gly Gly Gly Ser Gly Gly Gly Gly Ser Gly Gly Gly
        115                 120                 125

Gly Ser Leu Glu Gln Ile Gln Leu Val Gln Ser Gly Pro Glu Leu Lys
    130                 135                 140

Lys Pro Gly Glu Thr Val Lys Ile Ser Cys Lys Ala Ser Gly Tyr Thr
145                 150                 155                 160

Phe Thr Asp Tyr Pro Leu His Trp Val Lys Gln Ala Pro Gly Lys Gly
                165                 170                 175

Leu Gln Trp Met Ala Trp Ile Asn Thr Glu Thr Gly Glu Pro Thr Tyr
            180                 185                 190

Ala Asp Asp Phe Thr Gly Arg Phe Ala Phe Ser Leu Glu Thr Ser Ala
        195                 200                 205

Ser Thr Ala Tyr Leu Gln Ile Asn Asn Leu Lys Asn Glu Asp Thr Ala
    210                 215                 220

Thr Tyr Phe Cys Val Arg Gly Tyr Tyr Tyr Trp Gly Gln Gly Thr
225                 230                 235                 240

Thr Leu Ser Val Ser Ser Asp Tyr Lys Asp Asp Asp Lys
                245                 250

<210> SEQ ID NO 15
<211> LENGTH: 765
<212> TYPE: DNA
<213> ORGANISM: Artificial Sequence
```

<220> FEATURE:
<223> OTHER INFORMATION: Recombinantly produced polynucleotide encoding single chain antibody of SEQ ID NO:14 and STOP codon

<400> SEQUENCE: 15

```
atggacattg tgatgtcaca gtctccatcc tccctggctg tgtcagcagg agagaaggtc    60
actatgagct gcaaatccag tcagagtctg ctcaacagta gaacccgaaa gaataacttg   120
gcttggtacc agcagaaacc agggcagtct cctaaactgc tgatctactg ggcatccact   180
agggaatctg ggtccctga tcgcttcaca ggcagtggat ctgggacaga tttcactctc   240
accatcagca gtgtgcaggc tgaagacctg cagttttatt actgcaagca atcttataat   300
ctgtggacgt tcggtggagg caccaagctg gaaatcaaag tcgacggtgg tggtggttct   360
ggcggcggcg gctccggtgg tggtggttct ctcgagcaga tccagttggt gcagtctgga   420
cctgagctga agaagcctgg agagacagtc aagatctcct gcaaggcttc tggttatacc   480
ttcacagact atccattgca ctgggtgaag caggctccag aaagggtttt acagtggatg   540
gcctggataa acactgagac tggtgagcca acatatgcag atgacttcac gggacggttt   600
gccttctctt tggagacctc tgccagcact gcctatttgc agatcaacaa cctcaaaaat   660
gaggacacgg ctacatattt ctgtgttaga ggttattatt actactgggg ccaaggcacc   720
actctctcag tctcctcaga ctacaaagac gatgacgata aatag                   765
```

<210> SEQ ID NO 16
<211> LENGTH: 259
<212> TYPE: PRT
<213> ORGANISM: Artificial Sequence
<220> FEATURE:
<223> OTHER INFORMATION: Recombinantly produced single chain antibody

<400> SEQUENCE: 16

```
Gln Ala Gln Ile Gln Leu Val Gln Ser Gly Pro Glu Leu Lys Lys Pro
1               5                   10                  15

Gly Glu Thr Val Lys Ile Ser Cys Lys Ala Ser Gly Tyr Thr Phe Thr
            20                  25                  30

Asp Tyr Pro Leu His Trp Val Lys Gln Ala Pro Gly Lys Gly Leu Gln
        35                  40                  45

Trp Met Ala Trp Ile Asn Thr Glu Thr Gly Glu Pro Thr Tyr Ala Asp
    50                  55                  60

Asp Phe Thr Gly Arg Phe Ala Phe Ser Leu Glu Thr Ser Ala Ser Thr
65                  70                  75                  80

Ala Tyr Leu Gln Ile Asn Asn Leu Lys Asn Glu Asp Thr Ala Thr Tyr
                85                  90                  95

Phe Cys Val Arg Gly Tyr Tyr Tyr Trp Gly Gln Gly Thr Thr Leu
            100                 105                 110

Ser Val Ser Ser Gly Gly Gly Ser Gly Gly Gly Ser Gly Gly
        115                 120                 125

Gly Gly Ser Gly Gly Gly Ser Gly Gly Gly Ser Gly Gly Gly
            130                 135                 140

Gly Ser Asp Ile Val Met Ser Gln Ser Pro Ser Ser Leu Ala Val Ser
145                 150                 155                 160

Ala Gly Glu Lys Val Thr Met Ser Cys Lys Ser Ser Gln Ser Leu Leu
                165                 170                 175

Asn Ser Arg Thr Arg Lys Asn Asn Leu Ala Trp Tyr Gln Gln Lys Pro
            180                 185                 190

Gly Gln Ser Pro Lys Leu Leu Ile Tyr Trp Ala Ser Thr Arg Glu Ser
```

```
                195                 200                 205
Gly Val Pro Asp Arg Phe Thr Gly Ser Gly Ser Gly Thr Asp Phe Thr
            210                 215                 220

Leu Thr Ile Ser Ser Val Gln Ala Glu Asp Leu Ala Val Tyr Tyr Cys
225                 230                 235                 240

Lys Gln Ser Tyr Asn Leu Trp Thr Phe Gly Gly Gly Thr Lys Leu Glu
                245                 250                 255

Ile Lys Arg

<210> SEQ ID NO 17
<211> LENGTH: 777
<212> TYPE: DNA
<213> ORGANISM: Artificial Sequence
<220> FEATURE:
<223> OTHER INFORMATION: Recombinantly produced polynucleotide encoding
      single chain antibody of SEQ ID NO:16

<400> SEQUENCE: 17
caagcacaga tccagttggt gcagtctgga cctgagctga agaagcctgg agagacagtc     60
aagatctcct gcaaggcttc tggttatacc ttcacagact atccattgca ctgggtgaag    120
caggctccag gaaagggttt acagtggatg gcctggataa acactgagac tggtgagcca    180
acatatgcag atgacttcac gggacggttt gccttctctt tggagacctc tgccagcact    240
gcctatttgc agatcaacaa cctcaaaaat gaggacacgg ctacatattt ctgtgttaga    300
ggttattatt actactgggg ccaaggcacc actctctcag tctcctcagg tggtggtggt    360
tctggcggcg gcggctccgg tggtggtggt agcggcggtg tggttccgg cggcggcggc    420 tctggtggtg gtggttctga cattgtgatg tcacagtctc catcctccct ggctgtgtca    480
gcaggagaga aggtcactat gagctgcaaa tccagtcaga gtctgctcaa cagtagaacc    540
cgaaagaata acttggcttg gtaccagcag aaaccagggc agtctcctaa actgctgatc    600
tactgggcat ccactaggga atctggggtc cctgatcgct tcacaggcag tggatctggg    660
acagatttca ctctcaccat cagcagtgtg caggctgaag acctggcagt ttattactgc    720
aagcaatctt ataatctgtg gacgttcggt ggaggcacca agctggaaat caaacgt      777

<210> SEQ ID NO 18
<211> LENGTH: 263
<212> TYPE: PRT
<213> ORGANISM: Artificial Sequence
<220> FEATURE:
<223> OTHER INFORMATION: Recombinantly produced single chain antibody
      with C-terminal His tag

<400> SEQUENCE: 18

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Pro Leu His Trp Val Lys Gln Ala Pro Gly Lys Gly Leu Gln Trp Met
        35                  40                  45

Ala Trp Ile Asn Thr Glu Thr Gly Glu Pro Thr Tyr Ala Asp Asp Phe
    50                  55                  60

Thr Gly Arg Phe Ala Phe Ser Leu Glu Thr Ser Ala Ser Thr Ala Tyr
65              70                  75                  80

Leu Gln Ile Asn Asn Leu Lys Asn Glu Asp Thr Ala Thr Tyr Phe Cys
                85                  90                  95
```

Val Arg Gly Tyr Tyr Tyr Trp Gly Gln Gly Thr Thr Leu Ser Val
            100                 105                 110

Ser Ser Gly Gly Gly Ser Gly Gly Gly Ser Gly Gly Gly
        115                 120                 125

Ser Gly Gly Gly Ser Gly Gly Gly Ser Gly Gly Gly Ser
        130                 135                 140

Asp Ile Val Met Ser Gln Ser Pro Ser Ser Leu Ala Val Ser Ala Gly
145                 150                 155                 160

Glu Lys Val Thr Met Ser Cys Lys Ser Gln Ser Leu Leu Asn Ser
                165                 170                 175

Arg Thr Arg Lys Asn Asn Leu Ala Trp Tyr Gln Gln Lys Pro Gly Gln
            180                 185                 190

Ser Pro Lys Leu Leu Ile Tyr Trp Ala Ser Thr Arg Glu Ser Gly Val
        195                 200                 205

Pro Asp Arg Phe Thr Gly Ser Gly Ser Gly Thr Asp Phe Thr Leu Thr
    210                 215                 220

Ile Ser Ser Val Gln Ala Glu Asp Leu Ala Val Tyr Tyr Cys Lys Gln
225                 230                 235                 240

Ser Tyr Asn Leu Trp Thr Phe Gly Gly Gly Thr Lys Leu Glu Ile Lys
                245                 250                 255

Arg His His His His His His
            260

<210> SEQ ID NO 19
<211> LENGTH: 831
<212> TYPE: DNA
<213> ORGANISM: Artificial Sequence
<220> FEATURE:
<223> OTHER INFORMATION: Recombinantly produced construct encoding
      single chain antibody with restriction sites and His tag

<400> SEQUENCE: 19
taatacgtac aagcacagat ccagttggtg cagtctggac ctgagctgaa gaagcctgga      60
gagacagtca agatctcctg caaggcttct ggttatacct tcacagacta tccattgcac     120
tgggtgaagc aggctccagg aaagggttta cagtggatgg cctggataaa cactgagact     180
ggtgagccaa catatgcaga tgacttcacg ggacggtttg ccttctcttt ggagacctct     240
gccagcactg cctatttgca gatcaacaac ctcaaaaatg aggacacggc tacatatttc     300
tgtgttagag gttattatta ctactggggc caaggcacca ctctctcagt tcctcaggt     360 ggtggtggtt ctggcggcgg cggctccggt ggtggtggta gcggcggtgg tggttccggc     420
ggcggcggct ctggtggtgg tggttctgac attgtgatgt cacagtctcc atcctccctg     480
gctgtgtcag caggagagaa ggtcactatg agctgcaaat ccagtcagag tctgctcaac     540
agtagaaccc gaaagaataa cttggcttgg taccagcaga accagggcca gtctcctaaa     600
ctgctgatct actgggcatc cactagggaa tctggggtcc ctgatcgctt cacaggcagt     660
ggatctggga cagatttcac tctcaccatc agcagtgtgc aggctgaaga cctggcagtt     720
tattactgca agcaatctta taatctgtgg acgttcggtg gaggcaccaa gctggaaatc     780
aaacgtcatc atcatcatca tcatggaggt agttcttagg cggccgcata a             831

<210> SEQ ID NO 20
<211> LENGTH: 431
<212> TYPE: DNA
<213> ORGANISM: Artificial Sequence
<220> FEATURE:
<223> OTHER INFORMATION: Recombinantly produced construct encoding mouse antibody heavy chain variable region, with restriction
sites

<400> SEQUENCE: 20

```
cagaattcgt gatctagtcg acatggggttg ggtgtggaac ttgctattcc tgatggcagc    60
tgcccaatgt atccaagcac agatccagtt ggtgcagtct ggacctgagc tgaagaagcc   120
tggagagaca gtcaagatct cctgcaaggc ttctggttat accttcacag actatccatt   180
gcactgggtg aagcaggctc caggaaaggg tttacagtgg atggcctgga taaacactga   240
gactggtgag ccaacatatg cagatgactt cacgggacgg tttgccttct ctttggagac   300
ctctgccagc actgcctatt tgcagatcaa caacctcaaa aatgaggaca cggctacata   360
tttctgtgtt agaggttatt attactactg ggccaaggc accactctct cagtctcctc    420
agctagcgta t                                                       431
```

<210> SEQ ID NO 21
<211> LENGTH: 459
<212> TYPE: DNA
<213> ORGANISM: Artificial Sequence
<220> FEATURE:
<223> OTHER INFORMATION: Recombinantly produced construct encoding
mouse antibody light chain variable region, with restriction
sites

<400> SEQUENCE: 21

```
cacgaccggt ctagagctag cctaggctcg agaagcttgt cgacgaattc agatactagt    60
cgacatggtt ctcatgttac tgctgctatg ggtatctggt acctgtgggg acattgtgat   120
gtcacagtct ccatcctccc tggctgtgtc agcaggagag aaggtcacta tgagctgcaa   180
atccagtcag agtctgctca acagtagaac ccgaaagaat aacttggctt ggtaccagca   240
gaaaccaggg cagtctccta aactgctgat ctactgggca tccactaggg aatctggggt   300
ccctgatcgc ttcacaggca gtggatctgg gacagatttc actctcacca tcagcagtgt   360
gcaggctgaa gacctggcag tttattactg caagcaatct tataatctgt ggacgttcgg   420
tggaggcacc aagctggaaa tcaaacgtac ggatgctgc                          459
```

<210> SEQ ID NO 22
<211> LENGTH: 339
<212> TYPE: DNA
<213> ORGANISM: Artificial Sequence
<220> FEATURE:
<223> OTHER INFORMATION: Recombinantly produced polynucleotide encoding
mouse antibody light chain variable region

<400> SEQUENCE: 22

```
gacattgtga tgtcacagtc tccatcctcc ctggctgtgt cagcaggaga gaaggtcact    60
atgagctgca atccagtca gagtctgctc aacagtagaa cccgaaagaa taacttggct   120
tggtaccagc agaaaccagg gcagtctcct aaactgctga tctactgggc atccactagg   180
gaatctgggg tccctgatcg cttcacaggc agtggatctg gacagatttc actctcacc   240
atcagcagtg tgcaggctga agacctggca gtttattact gcaagcaatc ttataatctg   300
tggacgttcg gtggaggcac caagctggaa atcaaacgg                         339
```

<210> SEQ ID NO 23
<211> LENGTH: 342
<212> TYPE: DNA
<213> ORGANISM: Artificial Sequence
<220> FEATURE:
<223> OTHER INFORMATION: Recombinantly produced polynucleotide encoding mouse antibody heavy chain variable region

<400> SEQUENCE: 23

```
cagatccagt tggtgcagtc tggacctgag ctgaagaagc ctggagagac agtcaagatc    60
tcctgcaagg cttctggtta taccttcaca gactatccat tgcactgggt gaagcaggct   120
ccaggaaagg gtttacagtg gatggcctgg ataaacactg agactggtga gccaacatat   180
gcagatgact tcacgggacg gtttgccttc tctttggaga cctctgccag cactgcctat   240
ttgcagatca acaacctcaa aaatgaggac acggctacat atttctgtgt tagaggttat   300
tattactact ggggccaagg caccactctc tcagtctcct ca                       342
```

<210> SEQ ID NO 24
<211> LENGTH: 384
<212> TYPE: DNA
<213> ORGANISM: Artificial Sequence
<220> FEATURE:
<223> OTHER INFORMATION: Recombinantly produced polynucleotide encoding
      mouse antibody light chain variable region, with signal sequence

<400> SEQUENCE: 24

```
atggttctca tgttactgct gctatgggta tctggtacct gtggggacat tgtgatgtca    60
cagtctccat cctccctggc tgtgtcagca ggagagaagg tcactatgag ctgcaaatcc   120
agtcagagtc tgctcaacag tagaacccga aagaataact ggcttggta ccagcagaaa    180
ccagggcagt ctcctaaact gctgatctac tgggcatcca ctaggaatc tggggtccct    240
gatcgcttca caggcagtgg atctgggaca gatttcactc tcaccatcag cagtgtgcag   300
ctgaagacc tggcagtttta ttactgcaag caatcttata atctgtggac gttcggtgga    360
ggcaccaagc tggaaatcaa acgg                                            384
```

<210> SEQ ID NO 25
<211> LENGTH: 399
<212> TYPE: DNA
<213> ORGANISM: Artificial Sequence
<220> FEATURE:
<223> OTHER INFORMATION: Recombinantly produced polynucleotide encoding
      mouse antibody heavy chain variable region, with signal sequence

<400> SEQUENCE: 25

```
atgggttggg tgtggaactt gctattcctg atggcagctg cccaatgtat ccaagcacag    60
atccagttgg tgcagtctgg acctgagctg aagaagcctg gagagacagt caagatctcc   120
tgcaaggctt ctggttatac cttcacagac tatccattgc actgggtgaa gcaggctcca   180
ggaaagggtt tacagtggat ggcctggata aacactgaga ctggtgagcc aacatatgca   240
gatgacttca cgggacggtt tgccttctct ttggagacct ctgccagcac tgcctatttg   300
cagatcaaca acctcaaaaa tgaggacacg gctacatatt tctgtgttag aggttattat   360
tactactggg gccaaggcac cactctctca gtctcctca                            399
```

<210> SEQ ID NO 26
<211> LENGTH: 113
<212> TYPE: PRT
<213> ORGANISM: Artificial Sequence
<220> FEATURE:
<223> OTHER INFORMATION: Recombinantly produced antibody heavy chain
      variable region derived from mouse with native signal sequence
      removed and native C-terminal arginine residue removed;
      including an inserted N-terminal methionine residue

<400> SEQUENCE: 26

Met Asp Ile Val Met Ser Gln Ser Pro Ser Leu Ala Val Ser Ala
1               5                   10                  15

Gly Glu Lys Val Thr Met Ser Cys Lys Ser Ser Gln Ser Leu Leu Asn
            20                  25                  30

Ser Arg Thr Arg Lys Asn Asn Leu Ala Trp Tyr Gln Gln Lys Pro Gly
                35                  40                  45

Gln Ser Pro Lys Leu Leu Ile Tyr Trp Ala Ser Thr Arg Glu Ser Gly
        50                  55                  60

Val Pro Asp Arg Phe Thr Gly Ser Gly Ser Gly Thr Asp Phe Thr Leu
65                  70                  75                  80

Thr Ile Ser Ser Val Gln Ala Glu Asp Leu Ala Val Tyr Tyr Cys Lys
                85                  90                  95

Gln Ser Tyr Asn Leu Trp Thr Phe Gly Gly Gly Thr Lys Leu Glu Ile
            100                 105                 110

Lys

<210> SEQ ID NO 27
<211> LENGTH: 336
<212> TYPE: DNA
<213> ORGANISM: Artificial Sequence
<220> FEATURE:
<223> OTHER INFORMATION: Recombinantly produced polynucleotide encoding
      mouse antibody light chain variable region, without native signal
      sequence and without native C-terminal arginine residue

<400> SEQUENCE: 27
gacattgtga tgtcacagtc tccatcctcc ctggctgtgt cagcaggaga gaaggtcact      60
atgagctgca aatccagtca gagtctgctc aacagtagaa cccgaaagaa taacttggct     120
tggtaccagc agaaaccagg gcagtctcct aaactgctga tctactgggc atccactagg     180
gaatctgggg tccctgatcg cttcacaggc agtggatctg gacagattt cactctcacc      240 atcagcagtg tgcaggctga agacctggca gtttattact gcaagcaatc ttataatctg     300
tggacgttcg gtggaggcac caagctggaa atcaaa                               336

<210> SEQ ID NO 28
<211> LENGTH: 339
<212> TYPE: DNA
<213> ORGANISM: Artificial Sequence
<220> FEATURE:
<223> OTHER INFORMATION: Recombinantly produced polynucleotide encoding
      mouse antibody light chain variable region, without native signal
      sequence and without native C-terminal arginine residue; including
      an inserted N-terminal methionine residue

<400> SEQUENCE: 28
atggacattg tgatgtcaca gtctccatcc tccctggctg tgtcagcagg agagaaggtc      60
actatgagct gcaaatccag tcagagtctg ctcaacagta gaacccgaaa gaataacttg     120
gcttggtacc agcagaaacc agggcagtct cctaaactgc tgatctactg ggcatccact     180
agggaatctg ggtccctga tcgcttcaca ggcagtggat ctgggacaga tttcactctc      240
accatcagca gtgtgcaggc tgaagacctg gcagtttatt actgcaagca atcttataat     300
ctgtggacgt tcggtggagg caccaagctg gaaatcaaa                            339

<210> SEQ ID NO 29
<211> LENGTH: 5
<212> TYPE: PRT
<213> ORGANISM: Artificial Sequence
<220> FEATURE:
<223> OTHER INFORMATION: Synthesized linker segment

<400> SEQUENCE: 29

Gly Gly Gly Gly Ser
1               5

<210> SEQ ID NO 30
<211> LENGTH: 831
<212> TYPE: DNA
<213> ORGANISM: Artificial Sequence
<220> FEATURE:
<223> OTHER INFORMATION: Recombinantly produced construct encoding
      single chain antibody with restriction sites and His Tag;
      complementary strand to SEQ ID NO:19

<400> SEQUENCE: 30

```
ttatgcggcc gcctaagaac tacctccatg atgatgatga tgatgacgtt tgatttccag      60
cttggtgcct ccaccgaacg tccacagatt ataagattgc ttgcagtaat aaactgccag     120
gtcttcagcc tgcacactgc tgatggtgag agtgaaatct gtcccagatc cactgcctgt     180
gaagcgatca gggaccccag attccctagt ggatgcccag tagatcagca gtttaggaga     240
ctgccctggt ttctgctggt accaagccaa gttattcttt cgggttctac tgttgagcag     300
actctgactg gatttgcagc tcatagtgac cttctctcct gctgacacag ccagggagga     360
tggagactgt gacatcacaa tgtcagaacc accaccacca gagccgccgc cgccggaacc     420
accaccgccg ctaccaccac caccggagcc gccgccgcca gaaccaccac cacctgagga     480
gactgagaga gtggtgcctt ggccccagta gtaataataa cctctaacac agaaatatgt     540
agccgtgtcc tcattttga ggttgttgat ctgcaaatag gcagtgctgg cagaggtctc     600
caaagagaag gcaaaccgtc ccgtgaagtc atctgcatat gttggctcac cagtctcagt     660
gtttatccag gccatccact gtaaacectt tcctggagcc tgcttcaccc agtgcaatgg     720
atagtctgtg aaggtataac cagaagcctt gcaggagatc ttgactgtct ctccaggctt     780
cttcagctca ggtccagact gcaccaactg gatctgtgct tgtacgtatt a              831
```